US008638192B2

(12) United States Patent
Nagata

(10) Patent No.: US 8,638,192 B2
(45) Date of Patent: Jan. 28, 2014

(54) MONITORING NETWORK SYSTEM

(75) Inventor: Chihiro Nagata, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 1175 days.

(21) Appl. No.: 12/343,572

(22) Filed: Dec. 24, 2008

(65) Prior Publication Data
US 2009/0171169 A1 Jul. 2, 2009

(30) Foreign Application Priority Data

Dec. 26, 2007 (JP) ................. P.2007-333567

(51) Int. Cl.
H04Q 5/22 (2006.01)
G08B 1/08 (2006.01)
A61B 5/00 (2006.01)

(52) U.S. Cl.
USPC ............... 340/10.1; 340/10.5; 340/539.1

(58) Field of Classification Search
CPC ............ A61B 5/00; G06F 17/60; G08B 1/08; H04Q 5/22
USPC ............. 340/10.1–10.5, 539.1; 600/301, 300; 128/903; 455/8; 705/2, 3
See application file for complete search history.

(56) References Cited

U.S. PATENT DOCUMENTS

| 5,319,363 | A  | * | 6/1994  | Welch et al. ............ 340/8.1   |
| 6,616,606 | B1 | * | 9/2003  | Petersen et al. ......... 600/300   |
| 6,985,870 | B2 | * | 1/2006  | Martucci et al. ........... 705/3   |
| 7,038,588 | B2 | * | 5/2006  | Boone et al. .......... 340/573.1   |
| 7,384,410 | B2 | * | 6/2008  | Eggers et al. ............ 604/67   |
| 7,390,294 | B2 | * | 6/2008  | Hassler, Jr. .............. 600/37  |
| 7,411,506 | B2 | * | 8/2008  | Volpi et al. ........... 340/572.4  |
| 7,483,756 | B2 | * | 1/2009  | Engleson et al. .......... 700/83   |
| 7,609,145 | B2 | * | 10/2009 | Martis et al. ............ 340/5.1  |
| 7,683,759 | B2 | * | 3/2010  | Martis et al. .......... 340/5.83   |

(Continued)

FOREIGN PATENT DOCUMENTS

JP 4-266739 A 9/1992
JP 6-292657 A 10/1994

(Continued)

OTHER PUBLICATIONS

Japanese Office Action dated Mar. 5, 2010 in Japanese Application No. 2007-333567, 8 pages.
Japanese Office Action dated Nov. 9, 2010 in Japanese Application No. 2007-333567, (6 pages).

Primary Examiner — Nam V Nguyen
(74) Attorney, Agent, or Firm — Sughrue Mion, PLLC

(57) ABSTRACT

A monitoring network system includes: a plurality of monitoring apparatuses; and a remote monitoring apparatus, connected to the plurality of monitoring apparatuses. At least one of the monitoring apparatuses is configured to acquire biological signals from a patient and includes: a first holder, configured to hold a first ID; and a transmitter, configured to transmit the biological signal to the remote monitoring apparatus. The remote monitoring apparatus includes: a second holder, configured to hold a second ID and association information for associating a screen area in a display with the second ID; a detector, configured to detect the at least one of the monitoring apparatuses, when the first ID is identical with the second ID; a receiver, configured to receive the biological signal from the at least one of the plurality of monitoring apparatuses detected by the detector; and a display controller, configured to display the biological signal on the screen area in the display based on the association information.

17 Claims, 20 Drawing Sheets

(56) References Cited

U.S. PATENT DOCUMENTS

| | | | |
|---|---|---|---|
| 7,771,385 B2 * | 8/2010 | Eggers et al. | 604/65 |
| 7,774,852 B2 * | 8/2010 | Yokota et al. | 726/27 |
| 7,895,053 B2 * | 2/2011 | Holland et al. | 705/2 |
| 8,027,846 B2 * | 9/2011 | Schoenberg et al. | 705/2 |
| 8,058,986 B2 * | 11/2011 | Klabunde et al. | 340/539.12 |
| 8,308,640 B2 * | 11/2012 | Baldus et al. | 600/300 |
| 2005/0101844 A1 * | 5/2005 | Duckert et al. | 600/300 |

FOREIGN PATENT DOCUMENTS

| | | |
|---|---|---|
| JP | 7-163527 A | 6/1995 |
| JP | 2000-23925 A | 1/2000 |
| JP | 2001-128945 A | 5/2001 |
| JP | 2004-049309 A | 2/2004 |
| JP | 2004-536636 A | 12/2004 |
| JP | 2005-122339 A | 5/2005 |
| JP | 2007-229080 A | 9/2007 |

* cited by examiner

| SCREEN AREA | PATIENT UNIQUE ID | SCREEN AREA INFORMATION |
|---|---|---|
| E1 | #K0001 | UPPER LEFT POINT=(X1, Y1)<br>LOWER RIGHT POINT=(X2, Y2) |
| E2 | #K0002 | UPPER LEFT POINT=(X3, Y3)<br>LOWER RIGHT POINT=(X4, Y4) |
| ⋮ | ⋮ | ⋮ |
| E8 | #K0257 | UPPER LEFT POINT=(X15, Y15)<br>LOWER RIGHT POINT=(X16, Y16) |

FIG. 5

| No. | PATIENT UNIQUE ID | PATIENT INFORMATION ||||
| --- | --- | --- | --- | --- | --- |
| | | PATIENT NAME | IDENTIFICATION NUMBER | DATE OF BIRTH | FINGERPRINT INFORMATION |
| 1 | #K0001 | TARO KOHDEN | 123456 | 2000/01/01 | |
| 2 | #K0002 | JIRO KOHDEN | 987654 | 1985/05/05 | |
| ... | ... | ... | ... | ... | ... |
| 256 | #K0257 | YAKO KOHDEN | 13579 | 1995/10/10 | |

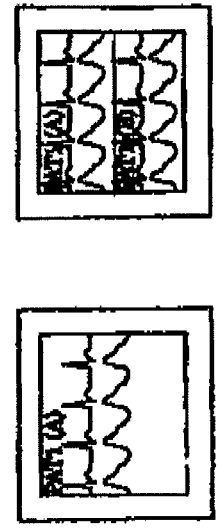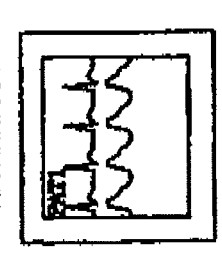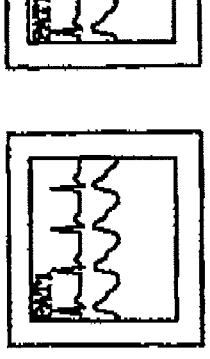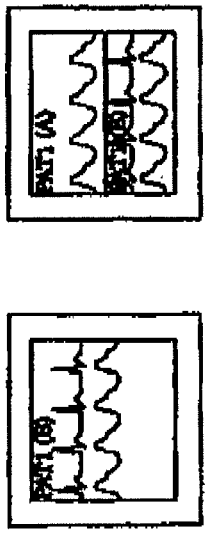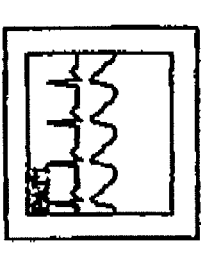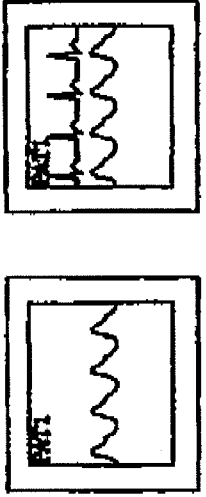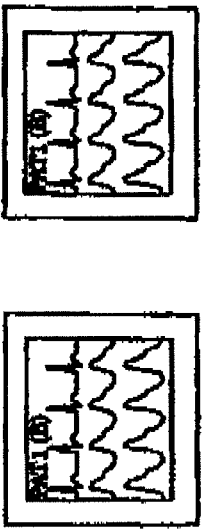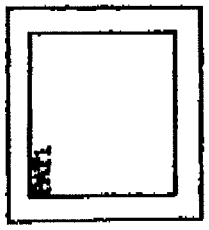
FIG. 12B

| No. | PATIENT UNIQUE ID | IDENTIFICATION INFORMATION OF PATIENT MONITORING APPARATUS | | |
|---|---|---|---|---|
| | | DEVICE NUMBER | LOCATION | COMMENTS |
| 1 | #K0001 | BED0001 | HOSPITAL WARD | IN HOSPITAL WARD |
| 2 | #K0002 | ICU0003 | ICU | IN ICU |
| 3 | #K0008 | TRN0008 | CONVEYING | BEING CONVEYED |
| . | . | . | . | . |
| . | . | . | . | . |
| . | . | . | . | . |
| 200 | #K0202 | BED0002 | HOSPITAL WARD | IN HOSPITAL WARD |
| 201 | #K0212 | OR0010 | OPERATING ROOM | IN OPERATION |
| 202 | #K0215 | EX0009 | EXAMINATION ROOM | IN EXAMINATION |

MONITORING NETWORK SYSTEM

BACKGROUND OF THE INVENTION

The present invention relates to a monitoring network system including: a plurality of patient monitoring apparatuses, such as blood pressure monitors, electrocardiogram monitors, bedside monitors, etc. connected to and acquiring biological signals from acquisition units, such as blood pressure sensors, electrocardiogram sensors, etc., that acquire the biological signals from a patient; a central monitor or other remote monitoring apparatus, displaying the biological signals on a display unit; and a network, connecting the patient monitoring apparatuses and the remote monitoring apparatus.

A related-art system is known with which a biological signal is transmitted from a monitor, disposed at a bedside and connected to an acquisition unit acquiring the biological signal from a patient, and a waveform display is performed, in accordance with the biological signal, on a video display screen disposed at a central station (see paragraph 0002 of JP-A-07-163527). Here, the biological signal displayed by the central station is transmitted from a monitor assigned in advance at the central station side (see paragraphs 0002 and 0003 of JP-A-04-266739).

There is also known a related-art system configured so that a biological signal of a patient being transported is collected to a centralized monitoring apparatus via a network to monitor the biological signal of the patient without interruption during the transport (see JP-A-2000-23925, especially paragraphs 0008 and 0009).

Furthermore, a related-art apparatus, carried by a patient and collecting a biological signal of the patient to perform seamless monitoring without interruption, has been developed (refer to "PCP apparatus" disclosed in JP-A-2004-536636).

However, with the related-art system disclosed in JP-A-04-266739, only a patient monitoring apparatus that has been selected in advance can be monitored. The related-art system disclosed in JP-A-2000-23925 is limited to performing seamless monitoring aiming at consolidated management of information, and in a case where all patient monitoring apparatuses are monitored, the centralized monitoring apparatus performing consolidated management is required to be extremely high in performance. Also the related-art system disclosed in JP-A-2004-536636 is premised on a patient using a specific measuring apparatus and does not accommodate for a case where the measuring apparatus itself is changed to a bedside monitor, etc., for the patient.

Thus when a patient is moved to another bed and measurements are to be made by another bedside monitor or other patient monitoring apparatus or when a patient is moved to an operating room and subject to surgery, unless a hospital ward or an attending physician in charge of caring for the patient re-assigns the appropriate patient monitoring apparatus with respect to the central monitor or other remote monitoring apparatus, the biological signal of the patient cannot be displayed in continuation. There was thus an issue that during the re-assigns process, patient monitoring is interrupted and the required monitoring cannot be performed. This is because a large number of monitors are present within a hospital and it is extremely difficult for medical staff to specify and input into the system which patient is being measured by which patient monitoring apparatus at a destination of patient movement.

SUMMARY

It is therefore an object of the invention to provide a monitoring network system, with which, even when acquisition of a biological signal of a patient is changed from a first patient monitoring apparatus, collecting the biological signal, to another, second patient monitoring apparatus, as long as the patient monitoring apparatuses appropriately hold a patient unique ID, a remote monitoring apparatus automatically selects or switches the patient monitoring apparatus monitored, thereby enabling monitoring of information by the biological signal continuously without interruption.

In order to achieve the object, according to the invention, there is provided a monitoring network system, comprising:
   a plurality of monitoring apparatuses; and
   a remote monitoring apparatus, connected to the plurality of monitoring apparatuses via network,
   wherein at least one of the plurality of monitoring apparatuses is configured to acquire biological signals from a patient and includes:
      a first holder, configured to hold a first ID and first information for identifying the patient which is associated with the first ID; and
      a transmitter, configured to transmit the biological signal to the remote monitoring apparatus, and
   wherein the remote monitoring apparatus includes:
      a second holder, configured to hold a second ID and association information for associating a screen area in a display with the second ID;
      a detector, configured to detect the at least one of the plurality of monitoring apparatuses whose the first holder holds the first ID, when the first ID is identical with the second ID;
      a receiver, configured to receive at least one of the biological signal and the first information from the at least one of the plurality of monitoring apparatuses detected by the detector; and
      a display controller, configured to display the at least one of the biological signal and the first information on the screen area in the display based on the association information.

The remote monitoring apparatus may include: a storage, configured to store the biological signals from the at least one of the plurality of monitoring apparatuses each of which holds the first ID; and a joiner, configured to join the stored biological signals in time series. The display controller may display the joined biological signals on the screen area in the display based on the association information.

The remote monitoring apparatus may include a central monitor including a computer.

The remote monitoring apparatus may includes: at least one server; and a remote viewer terminal. The at least one server may include: an identifier, configured to specify the first ID based on the first information; and the detector.

Each of the plurality of monitoring apparatus may include a notifier, configured to transmit, to the remote monitoring apparatus, a notification to notify a state in which the each of the plurality of monitoring apparatus is disable to acquire the biological signal. After receiving the notification from the at least one of the plurality of monitoring apparatuses whose the first holder holds the first ID, the remote monitoring apparatus may start to perform a detection operation for detecting the at least one of the plurality of monitoring apparatuses whose the first holder holds the first ID.

When the receiver receives the biological signals from the at least one of the plurality of monitoring apparatuses each of which holds the first ID, the display controller may display only one of the received biological signals.

When the receiver receives the biological signals from the at least one of the plurality of monitoring apparatuses each of which holds the first ID, the display controller may display at least one of the biological signals.

The display controller may display second information for identifying the at least one of the plurality of monitoring apparatuses from which the receiver receives the biological signal, together with the at least one of the biological signal and the first information.

BRIEF DESCRIPTION OF THE DRAWINGS

FIG. 5 is an example of information stored in a database of the central monitor, constituting the monitoring network system according to the first embodiment of the present invention.

FIG. 12B is a diagram of a last half of examples of variation with time of displays in respective monitors when the operation according to the patient monitoring apparatus switching display function of the central monitor, constituting the monitoring network system according to the first embodiment of the present invention, is performed.

DETAILED DESCRIPTION OF PREFERRED EMBODIMENTS

Figure 1:
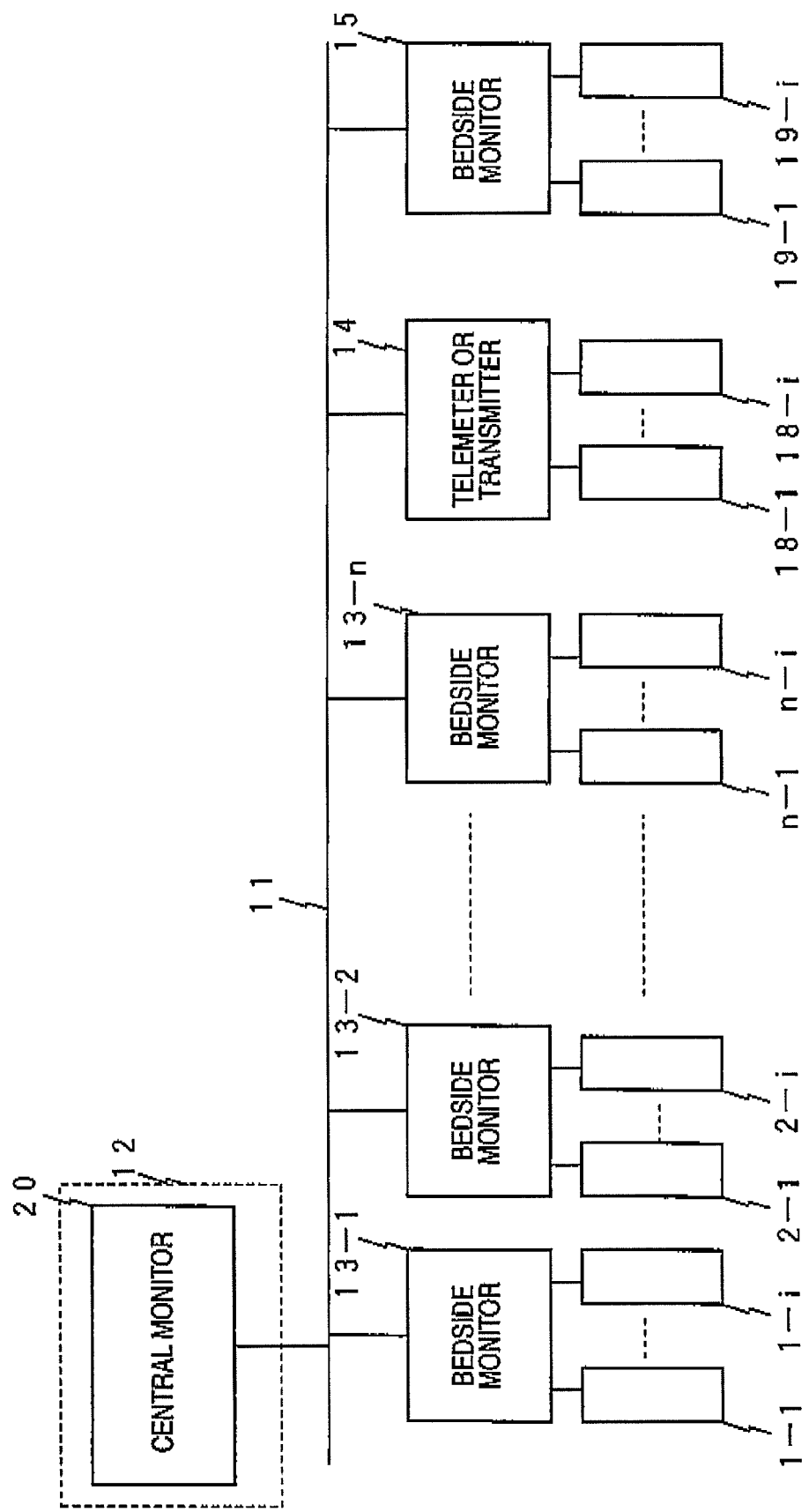
FIG. 1 is a block diagram of a monitoring network system according to a first embodiment of the present invention.

Embodiments of a monitoring network system according to the present invention shall now be described with reference to the attached drawings. In the drawings, components that are the same shall be provided with a same symbol and redundant description shall be omitted.

First Embodiment

As shown in FIG. 1, a monitoring network system according to a first embodiment includes: a network 11; a remote monitoring apparatus 12, displaying a signal waveform based on a biological signal on a display unit; bedside monitors 13-1 to 13-n, which are a plurality of patient monitoring apparatuses connected to and acquiring biological signals from blood pressure sensors, electrocardiogram sensors, or other acquisition units 1-1 to 1-i, 2-1 to 2-i, ..., n-1 to n-i, 18-1 to 18-i, and 19-1 to 19-i that acquire biological signals from a patient; a telemeter OR transmitter 14; and a bedside monitor 15. Here, each apparatus indicated as a bedside monitor may be an apparatus that measures a single parameter, such as a blood pressure monitor, an electrocardiogram monitor, etc.

Figures 2, 3:
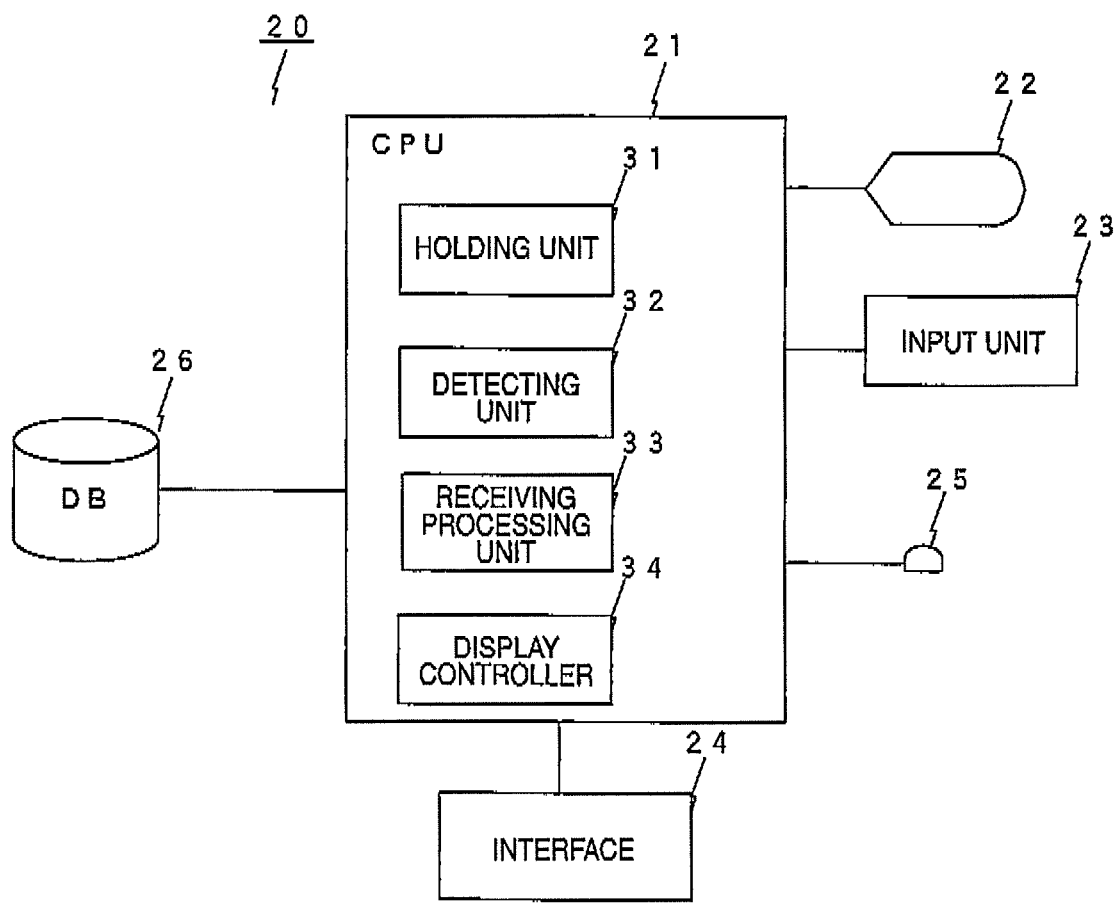
FIG. 2 is a block diagram of a central monitor, constituting the monitoring network system according to the first embodiment of the present invention.
FIG. 3 is a diagram of an example of information held in a holding unit of the central monitor, constituting the monitoring network system according to the first embodiment of the present invention.

Here, the remote monitoring apparatus 12 is a central monitor 20, mainly constituted of a CPU 21 and including a display unit 22, constituted of an LCD, etc., a input unit 23, constituted of a keyboard, touch panel, etc., and an interface 24, connected to the network 11, as main components as shown in FIG. 2.

The present embodiment may also include a scanner 25, for performing scanning, etc. for inputting patient identification information unique to each patient. The scanner 25 is generally a unit for inputting patient identification information and may be a camera, an image reading device, or a reader, reading an IC tag worn by a patient or a consultation card, indicating an ID number, etc. As the patient identification information, an image of a fingerprint, a blood vessel pattern of a palm, etc., a luster, or a face, etc., may be used.

Patient identification information is also input from the input unit 23. The patient identification information input here includes, for example, a name, ID number, date of birth, time of admission, etc. Furthermore, the patient identification information may be input manually from the input unit 23 instead of using the scanner 25 or may be input from any of various types of cards. Inputting may also be made to provide the information via the network 11. An electrocardiogram waveform or other biological signal may be used as the patient identification information, and in a case of employing such a configuration, it suffices that the configuration enable input of the biological signal, and an electrocardiogram monitor may be used.

A DB 26 holds the patient identification information input via the scanner 25, the input unit 23, and the interface 24, a patient unique ID for specifying the patient, and an association of the patient unique ID and the patient identification information as shown in FIG. 5. The patient unique ID is generated when the patient identification information of a new patient is input, and the patient unique ID may be the patient identification information itself, may be generated by combining, editing, or converting the patient identification information, may be any ID generated in a non-overlapped manner by the CPU 21 or a CPU 41, or may be delivered by an apparatus generating patient unique IDs or a member storing patient unique IDs. The CPU 21 has a function of using the DB 26 to search held information based on input patient identification information and thereby specifying the patient unique ID.

For input of the patient unique ID into a patient monitoring apparatus, the ID may be input directly from the patient monitoring apparatus side or may be input from the remote monitoring apparatus 12 and delivered to the patient monitoring apparatus.

Figure 4A:
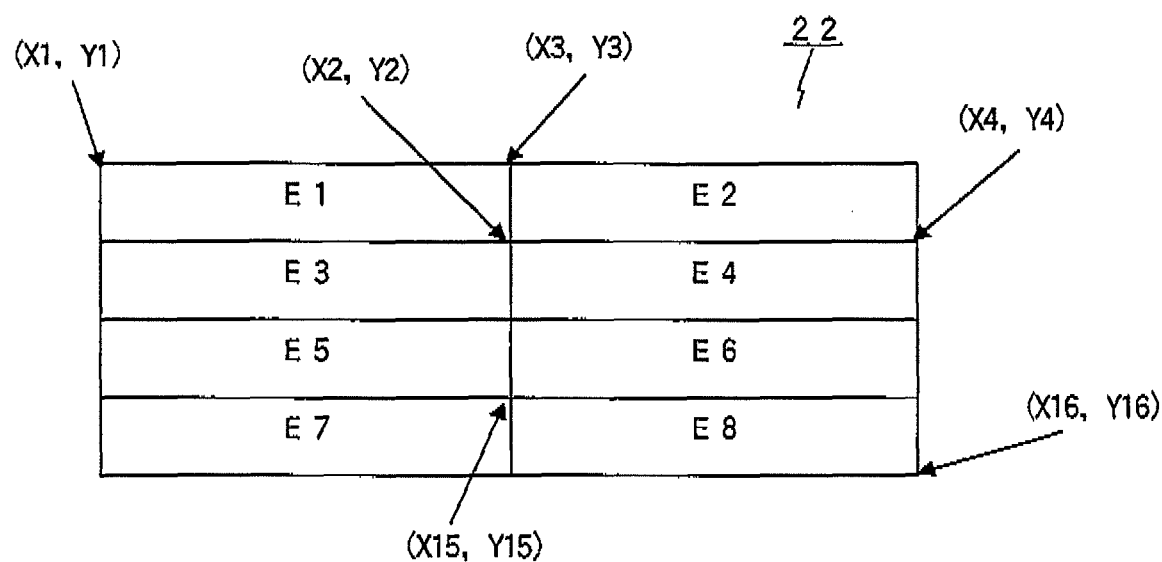
FIG. 4A is a diagram of an example of a screen of a display unit when patient unique IDs are set in association with display regions in the monitoring network system according to the present invention.

The CPU 21 includes a holding unit 31, a detecting unit 32, a receiving processing unit 33, and a display controller 34. The holding unit 31 holds information on association of a screen area in the display unit 22, in which biological information, such as a waveform, measured value, etc., based on a biological signal of the patient, is displayed, with the patient unique ID, and for example, the patient unique ID and position information on a screen of the display unit 22 are stored as shown in FIG. 3. A position and size of the area, in which the waveform based on the biological signal of the patient is displayed, are thereby specified (FIG. 4A). In regard to the information of the holding unit 31, for example, eight area sections E1 to E8 may be displayed on the display unit 22 as shown in FIG. 4A as a screen for setting the association of the patient unique ID and the screen area, any of the sections E1 to E8 may be selected via a touch panel, and the holding unit 31 may be made to hold a patient unique ID by input of the patient identification information from the input unit 23.

Figure 4B:
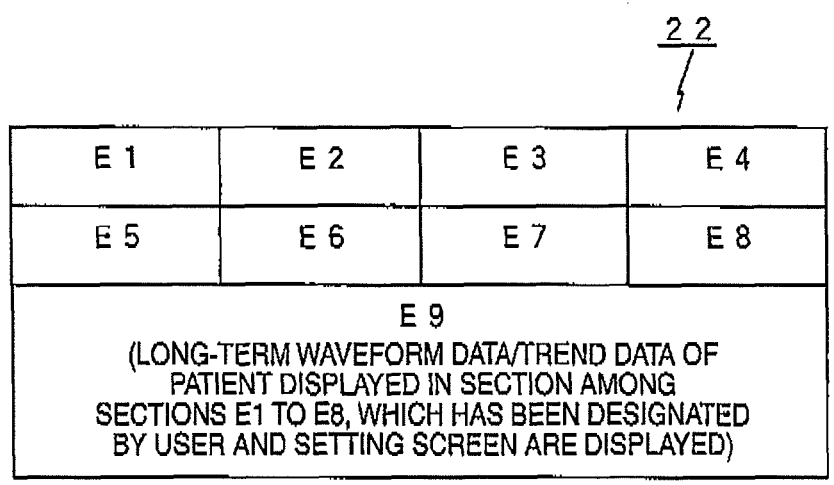
FIG. 4B is a diagram of another example of the screen of the display unit when patient unique IDs are set in association with display regions in the monitoring network system according to the present invention.

The position and size of the screen area may be enabled to be changed upon receiving an instruction input from a user by preparing and storing a plurality of screen area types and the display may be changed, for example as shown in FIG. 4B, according to a command from the CPU 21 that has received the instruction input from the user. With the example of FIG. 4B, the screen area is divided into two stages of an upper stage and a lower stage, the upper stage is divided further into two stages, with the sections E1 to E4 being displayed in an upper stage and the sections E5 to E8 being displayed in a lower stage, and in a section E9, occupying half of the entirety, long-term waveform data/trend data of a patient, displayed in a section among the sections E1 to E8 that has been designated by the user, or a setting screen is displayed.

Based on patient unique IDs outputted from the respective bedside monitors 13-1 to 13-n, the telemeter OR transmitter 14, and the bedside monitor 15, the detecting unit 32 detects a patient monitoring apparatus holding a same patient unique ID as a patient unique ID held in the holding unit 31.

The receiving processing unit 33 receives transmission of a biological signal and patient identification information from the patient monitoring apparatus, among the respective bedside monitors 13-1 to 13-n, the telemeter OR transmitter 14, and the bedside monitor 15, that has been detected by the detecting unit 32. The display controller 34 displays both or either of the biological signal and the patient identification information based on the received signal on the corresponding screen area of the display unit 22 based on the information held in the holding unit 31. The received patient identification information may also be used by the CPU 21 using the DB 26 to specify the patient unique ID. The specified patient unique ID is transmitted via the interface 24 to the bedside monitor, etc., which is the transmission source, and used by the bedside monitor, etc., to specify the patient.

Figure 6:
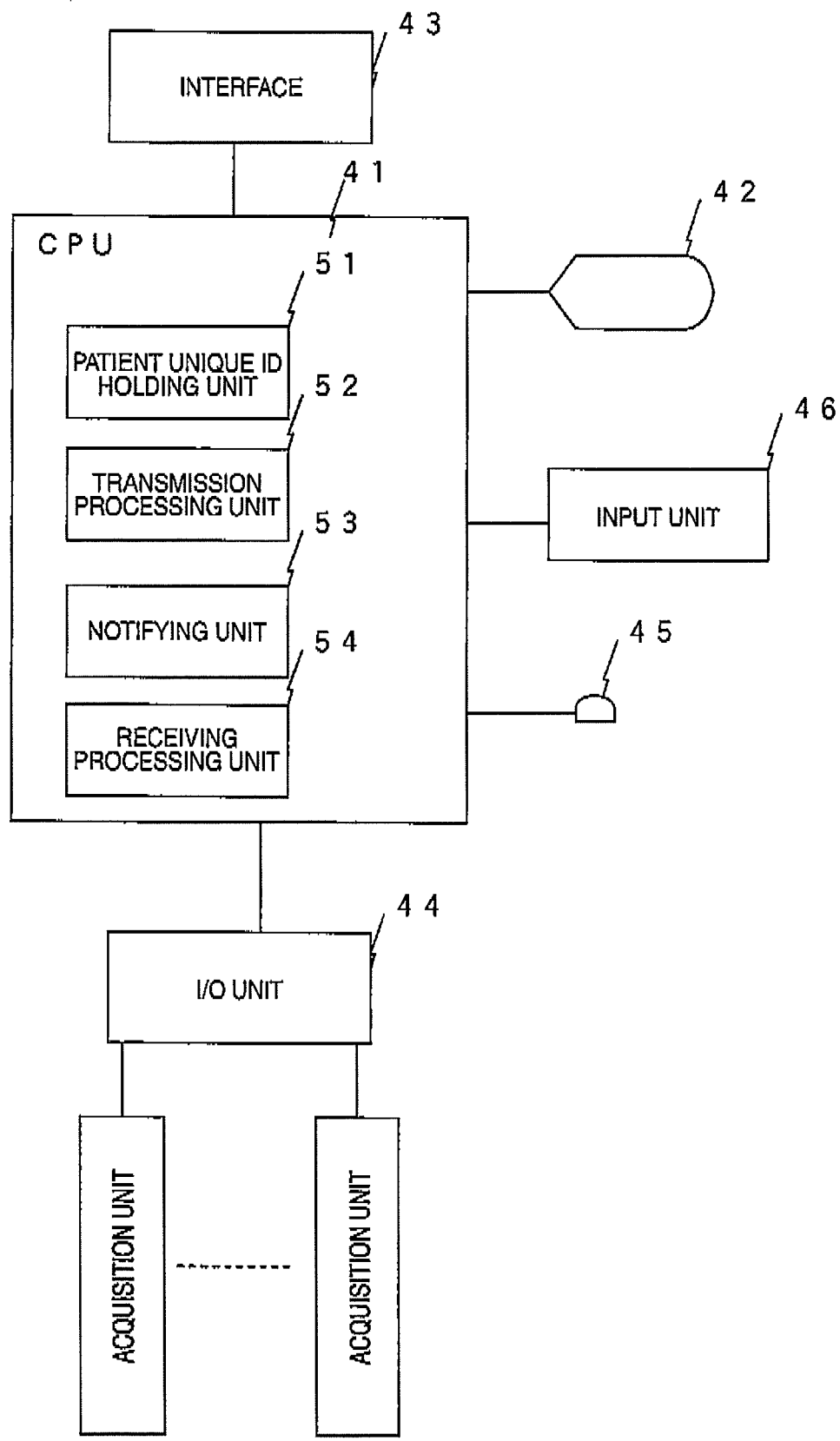
FIG. 6 is a block diagram of a bedside monitor, constituting the monitoring network system according to the first embodiment of the present invention.

Each of the bedside monitors 13-1 to 13-n shown in FIG. 1 is a bedside monitor disposed for example in a general ward, the telemeter OR transmitter 14 is used, for example, when a patient is to be transferred to another location, and the bedside monitor 15 is disposed, for example, in an operating room, examination room, etc. Each of the bedside monitors 13-1 to 13-n and the bedside monitor 15 is configured as shown in FIG. 6. That is, each monitor is mainly constituted of a CPU 41 and includes a display unit 42, constituted of an LCD, etc., an interface 43, connected to a network 11, and an I/O unit 44, taking in biological signals from the blood pressure sensors, electrocardiogram sensors, or other acquisition units 1-1 to 1-i, 2-1 to 2-i, ..., n-1 to n-i, and 19-1 to 19-i, as main components.

Each of the bedside monitors 13-1 to 13-n and the bedside monitor 15 may have a touch panel or other input unit for inputting patient identification information. Furthermore, each may include a scanner 45 for performing scanning etc., for taking in the patient identification information. The scanner 45 is a unit for inputting the patient identification information and corresponds to the scanner 25 described using FIG. 2.

Each CPU 41 includes a patient unique ID holding unit 51, a transmission processing unit 42, a notifying unit 53, and a receiving processing unit 54. The patient unique ID holding unit 51 holds the patient unique ID.

The transmission processing unit 52 performs, on the biological signals acquired from the acquisition units 1-1 to 1-i, 2-1 to 2-i, . . . , n-1 to n-i, and 19-1 to 19-i, conversion to signals to be transmitted through the network 11 and transmits the signals to the network 11. The transmission processing unit 52 also transmits the patient identification information, input from the input unit 46, the scanner 45, or an acquisition unit, to the remote monitoring apparatus 12 via the network 11. The CPU 41 also has a function of displaying, on the display unit 42, biological information based on the biological signals acquired from the acquisition units 1-1 to 1-i, 2-1 to 2-i, . . . , n-1 to n-i, and 19-1 to 19-i.

The receiving processing unit 54 receives a patient unique ID that is obtained by searching the DB 26 of the remote monitoring apparatus 12 using the patient identification information transmitted by the transmitting processing unit 52. The received patient unique ID is held in the patient unique ID holding unit 51.

The notifying unit 53 detects and notifies predetermined states, including at least non acquirable state which is a state where biological signal acquisition by the acquisition units 1-1 to 1-i, 2-1 to 2-i, . . . , n-1 to n-i, and 19-1 to 19-i is disabled. Here, the predetermined states including the non acquirable state are the states of disconnect electrode, disconnect probe, disconnect connector, suspend monitoring (temporary leaving of bed), etc. Although a state of turning on of power is not the non acquirable state, it is included among the predetermined states and is notified. A state, where a process according to a patient monitoring apparatus switching display function (display function by changeover of patient monitoring apparatus), to be described later, is performed, that is, a state, where a presence of a second patient monitoring apparatus, acquiring biological signals from a single patient corresponding to the same patient identification information, is detected, is also included among the predetermined states. Although when power is turned off, this is not notified, biological signal acquisition is disabled at the central monitor 20 and the same process as that performed upon notification is performed in this case.

The telemeter OR transmitter 14 shown in FIG. 1 is a patient monitoring apparatus that is connected wirelessly to the network 11 and unlike the bedside monitors 13-1 to 13-n and 15, may not have the display unit 42.

Figure 7:
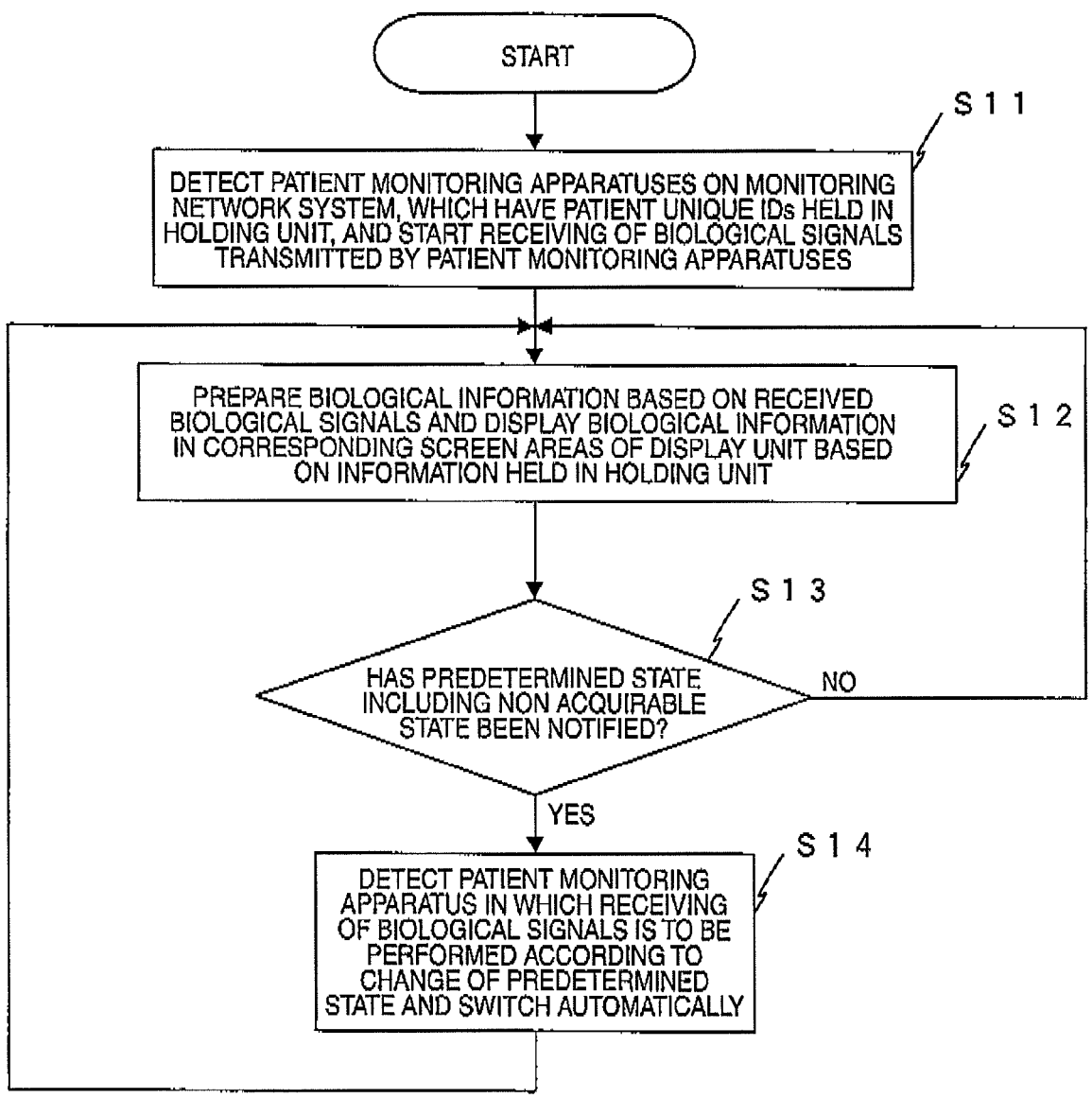
FIG. 7 is a flowchart for describing an operation of the central monitor, constituting the monitoring network system according to the first embodiment of the present invention.

With the monitoring network system configured as described above, because when an instruction to perform multi monitor display of a plurality of patients is provided at the central monitor 20, the CPU 21 operates by using a program corresponding to a flowchart shown in FIG. 7 for each screen area to thereby realize the respective units of FIG. 2, the operation shall be described based on FIG. 7. Before the instruction to perform multi monitor display of the patients is provided, the process of associatedly storing the patient unique ID and the position information on the screen of the display unit 22 in the holding unit 31 is performed as was described using FIGS. 3 and 4. The registration of the patient unique ID by the input unit or the scanner 45 is performed at each of the bedside monitors 13-1 to 13-n, the telemeter OR transmitter 14, and the bedside monitor 15 that perform collection of biological signals.

When the instruction to perform monitor display is provided, the central monitor 20 detects, according to each of the screen areas (eight screen areas in the present case), the patient monitoring apparatus among the bedside monitors 13-1 to 13-n, the telemeter OR transmitter 14, and the bedside monitor 15 with which the patient unique ID held in the patient unique ID holding unit 51 matches and starts receiving the biological signals transmitted from the detected patient monitoring apparatus (S11).

In continuation from step S11, the transmission of the signal, converted from the biological signal and transmitted through the network 11 by the transmission processing unit 52 of each specified patient monitoring apparatus (among the bedside monitors 13-1 to 13-n, the telemeter OR transmitter 14, and the bedside monitor 15), is received and both or either of the biological signal and the patient identification information based on this signal is or are prepared and displayed in the corresponding screen area of the display unit 22 based on the information held in the holding unit 31 (S12). In this case, a monitor name, a monitor installation location (hospital room number and patient bed number) and a control department, which are identification information specifying the patient monitoring apparatus acquiring the biological signal corresponding to a displayed waveform, and a patient name held in the holding unit 31 or the DB 26, etc., are displayed in association with the waveform.

Whether or not notification of a predetermined state, including the non acquirable state, is made is then detected (S13). If a notification is not detected, step S12 is returned to and the biological information display process is continued. If a notification is made, receiving of biological signals from unnecessary patient monitoring apparatuses is stopped in accordance with a change of a predetermined state, the necessary patient monitoring apparatuses are detected, and the receiving of biological signals from the detected patient monitoring apparatuses is started anew (S14). A return to step S12 is then performed and the process is continued.

Figure 8:
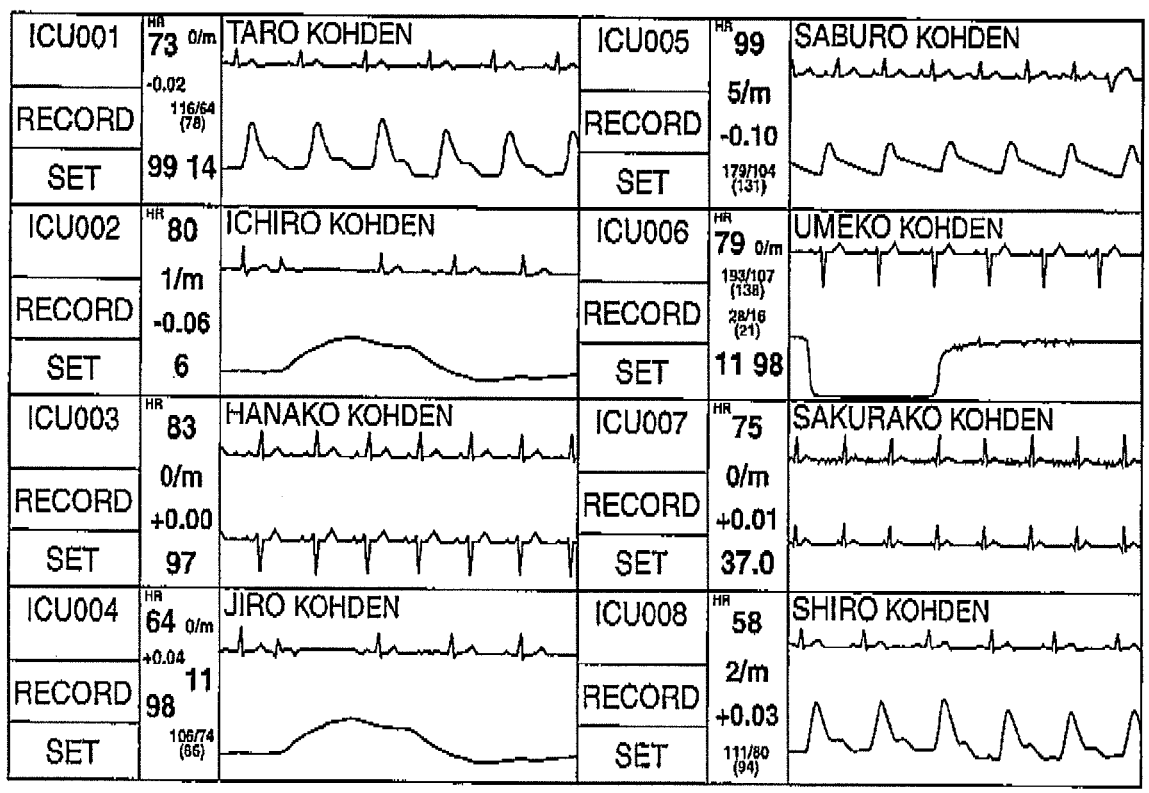
FIG. 8 is a photograph serving as a diagram of an example of a waveform display corresponding to biological signals displayed in the central monitor, constituting the monitoring network system according to the first embodiment of the present invention.

An example of a waveform display displayed on the display unit 22 by the above process is shown in FIG. 8. In each of the eight area sections E1 to E8 in the display unit 22, waveforms based on biological signals corresponding to a registered patient are displayed and a patient name (Taro Kohden in section E1), which is as one type of patient identification information, and monitor identification information (ICU0001) are displayed additionally. Here, even when the patient name (Taro Kohden) is transferred from the patient monitoring apparatus of the monitor identification information (ICU0001) to the patient monitoring apparatus of the monitor identification information (ICU0011) and measurements are made, waveforms based on the biological signals corresponding to the patient name (Taro Kohden) are displayed in the same section E1. Because the patient monitoring apparatuses are switched in this case, the patient name (Taro Kohden) and the new monitor name (for example, ICU0011) are displayed additionally in the section E1.

During progress of the process corresponding to the flowchart shown in FIG. 7, the CPU 21 stores the biological signals received from the patient monitoring apparatuses in a storage unit, such as the DB 26, and the CPU 21 and the DB 26 or other storage unit functions as a biological signal storing unit that stores the biological signals received from the patient monitoring apparatuses. When while a display such as that shown in FIG. 8 is being performed, an instruction for changing the display as shown in FIG. 4B is inputted by a user, the CPU 21 detects the position and size information of the screen area and the patient unique IDs associated with the respective sections from information set in advance and, based on which of the sections E1 to E8 the user designated, detects the biological signals of the patient unique ID to be displayed in the section E9. The CPU 21 displays, in the sections E1 to E8, the waveforms based on the biological signals corresponding to the patient unique IDs set in advance. The CPU 21 also operates as a biological signal joining unit that joins the biological signals (held by the biological signal storing unit) to be displayed in the section E9 in time series.

The CPU 21 furthermore functions as a review display unit, displaying the joined biological signals in the screen area (E9 in the present case) based on the designation by the user. Long-term waveform data/trend data, for example, of the patient displayed in the section E2 and a setting screen can thereby be displayed in the section E9. The function of the CPU 21 described here is also realized by a CPU 71 of remote viewer terminals 70-1 and 70-2 to be described later. Although here, the biological signals of the patient unique ID to be displayed in the section E9 are detected based on which of the sections E1 to E8 the user designated, one of the sections E1 to E8 may be selected in advance and the biological signals of the patient unique ID to be displayed in the section E9 may be detected based on this selection. Obviously, if the CPU 21 is not instructed to change the display as shown in FIG. 4B, the review display unit may perform display in the area set from the beginning (E2 in the present example).

<Patient Monitoring Apparatus Switching Display Function (Display Function by Changeover of Patient Monitoring Apparatus)>

To accommodate a case where the detecting unit 32 detects a plurality of patient monitoring apparatuses acquiring biological signals corresponding to the same patient unique ID, the receiving processing unit 33 in the CPU 21 of the central monitor 20 receives biological signals transmitted from the transmission processing unit 52 of a single patient monitoring apparatus among the patient monitoring apparatuses and the display controller 34 has a function (hereinafter, single screen function) of displaying biological information generated from the received signals in the screen area of the display unit 22 associated with the patient unique ID. Also in the case where the detecting unit 32 detects a plurality of patient monitoring apparatuses acquiring biological signals corresponding to the same patient unique ID, the receiving processing unit 33 in the CPU 21 receives biological signals transmitted from the transmission processing units 52 of two or more patient monitoring apparatuses among the patient monitoring apparatuses and the display controller 34 has a function (hereinafter, multiple screen function) of comprehensively displaying the biological information generated from the received signals in the screen area of the display unit 22 associated with the patient unique ID. The single screen function and the multiple screen function are referred to collectively as the patient monitoring apparatus switching display function (display function by changeover of patient monitoring apparatus).

This function is used, for example, when a patient is transported in a hospital, to perform seamless monitoring using a bedside monitor or other patient monitoring apparatus A, collecting biological signals of the patient from the beginning, and a telemeter OR transmitter or other patient monitoring apparatus B for collecting the biological signals of the patient during conveying and furthermore at the conveying destination. That is, the present function is used when, while acquisition by the patient monitoring apparatus A at a transport origin is enabled, an acquisition unit, such as electrodes and other sensor portions of a blood pressure monitor, electrocardiogram monitor, etc., connected to the patient monitoring apparatus B of the transport destination are set simultaneously on the patient to enable collection by the patient monitoring apparatus B.

Although in the case of the single screen function, biological information, corresponding to the biological signals acquired by just one of either of the patient monitoring apparatuses A and B of the above example, is displayed, eventually the blood pressure sensor, electrocardiogram sensor, and other acquisition units connected to the apparatus A, become removed from the patient. In this case, in regard to at what timing the waveforms corresponding to the biological signals acquired by the patient monitoring apparatus B are to be displayed, biological signals that are important in terms of monitoring (important parameters) are set and registered in advance, for example, according to each patient, and the switching of display may be performed at a timing at which a registered important parameters becomes no longer acquired from the patient monitoring apparatus (the patient monitoring apparatus A in the present case) corresponding to the blood pressure sensor, electrocardiogram sensor, and other acquisition units that are set on the patient at first. Obviously, the switching of display may instead be performed at a timing at which the stored important parameter becomes acquired from patient monitoring apparatus (the patient monitoring apparatus B in the present case) corresponding to the blood pressure sensor, electrocardiogram sensor, and other acquisition units that are set on the patient later. Furthermore, the switching of display may be performed at a timing at which an important parameter becomes no longer included in the biological signals of the already selected patient monitoring apparatus A and the important parameter becomes measured among the biological signals of the other patient monitoring apparatus B.

Figure 9:
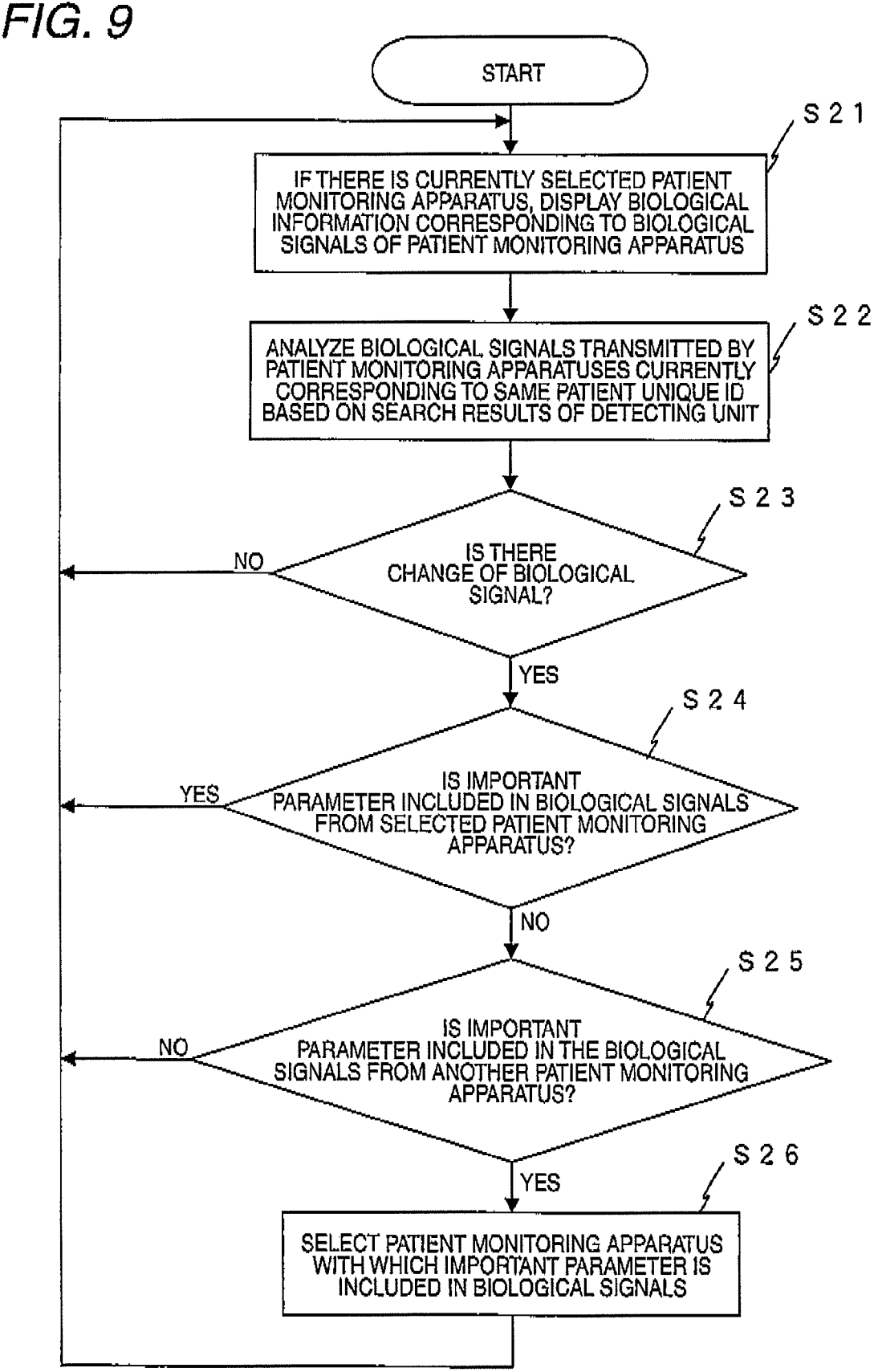
FIG. 9 is a flowchart for describing an operation according to a patient monitoring apparatus switching display function of the central monitor, constituting the monitoring network system according to the first embodiment of the present invention.

FIG. 9 is a flowchart of the process by the single screen function, and an operation according to the single screen function shall now be described based on this flowchart. In a state, not immediately after starting, where a patient monitoring apparatus (any of bedside monitors 13-1 to 13-n, the telemeter OR transmitter 14, and the bedside monitor 15) is already selected, display of biological information corresponding to biological signals from the patient monitoring apparatus is performed (S21), the biological signals of the plurality of patient monitoring apparatuses corresponding to the same patient unique ID are analyzed according to the detection results of the detecting unit 32 (S22), and whether or not there is a change, such as start or end of measurement, in regard to the biological signals corresponding to the patient in question, is determined (S23).

Whereas if in step S23, there is no change related to the biological signals, step S21 is returned to and the process there is performed, if in step S23, a change related to the biological signals is confirmed, whether or not an important parameter, set in advance, is included among the biological signals from the patient monitoring apparatus, selected in step S21, is analyzed (S24).

Whereas if in step S24, it is confirmed that an important parameter is included, step S21 is returned to and the process there is performed, if in step S24, it is confirmed that an important parameter is not included, whether or not an important parameter is included among the biological signals of another, non-selected patient monitoring apparatus is analyzed (S25).

If in step S25, it is confirmed that an important parameter is included among the biological signals of another, non-selected patient monitoring apparatus, this device is set as a newly selected patient monitoring apparatus (S26) and step S21 is returned to and the process there is performed. If in step S25, it cannot be confirmed that an important parameter is included among the biological signals of another, non-selected patient monitoring apparatus, step S21 is returned to and the process there is performed. By such a process, when an important parameter becomes no longer among the biological signals of the already-selected patient monitoring apparatus and the important parameter becomes measured among the biological signals of the other patient monitoring apparatus, the patient monitoring apparatus measuring the important parameter is selected anew and the biological information from the biological signals of the newly selected device becomes displayed. Thus even in a case where a patient monitoring apparatus is exchanged or replaced, seamless monitoring of the biological information corresponding to the biological signals related to a desired patient is enabled with a number of times of switching of the displayed biological information being minimized.

Figure 10:
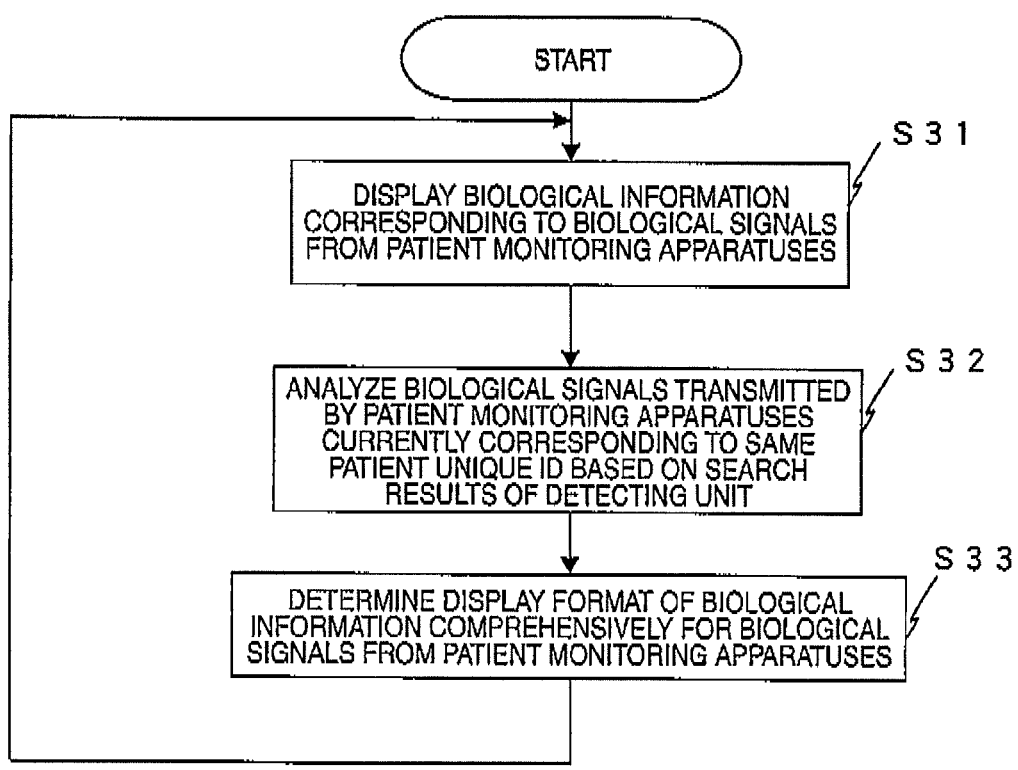
FIG. 10 is a flowchart for describing an operation according to the patient monitoring apparatus switching display function of the central monitor, constituting the monitoring network system according to the first embodiment of the present invention.

FIG. 10 is a flowchart of the process by the multiple screen function and an operation according to the multiple screen function shall now be described based on this flowchart. Display of biological information corresponding to the currently acquired biological signals from the patient monitoring apparatuses is performed (S31), the presence of a plurality of patient monitoring apparatuses transmitting the biological signals corresponding to the same patient unique ID is analyzed based on the detection results of the detecting unit 32 (S32), and a biological information display format is determined comprehensively for the biological signals (S33). Thereafter step S31 is returned to and display is performed again according to the determined display format.

"DETERMINE DISPLAY FORMAT OF BIOLOGICAL INFORMATION COMPREHENSIVELY FOR BIOLOGICAL SIGNALS" in step S33 means to determine the display format according to types of the arriving biological signals and a number of the patient monitoring apparatuses transmitting the arriving biological signals. Specifically, if the number of patient monitoring apparatuses transmitting the arriving biological signals is two, display is performed upon dividing the display screen into two, it the number of patient monitoring apparatuses transmitting the arriving biological signals is three, display is performed upon dividing the display screen into three, and in general, if the number of patient monitoring apparatuses transmitting the arriving biological signals is N, display is performed upon dividing the display screen into N sections.

Figure 11A:
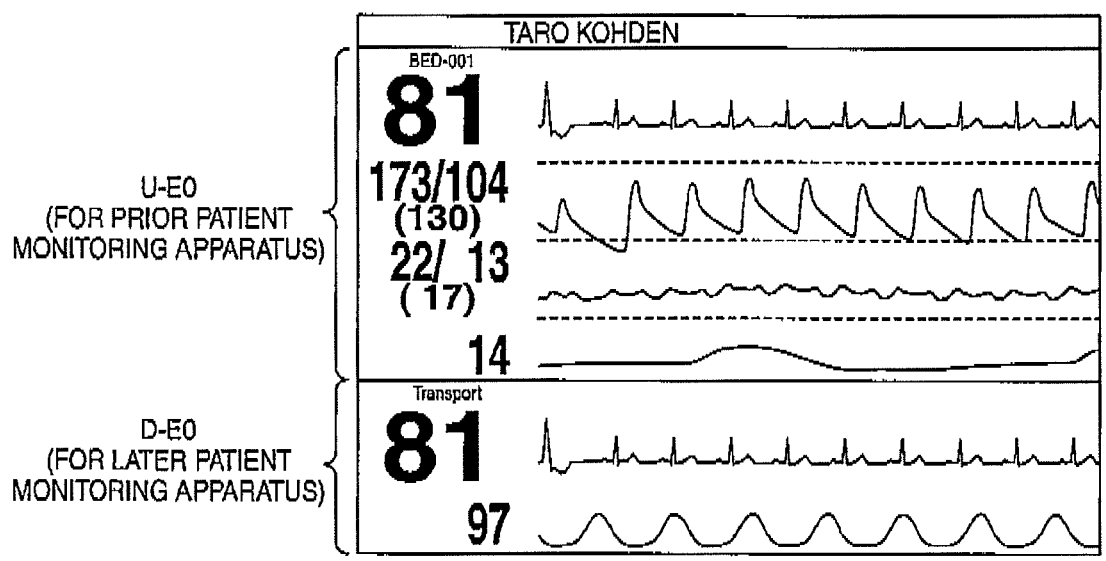
FIG. 11A is a photograph serving as a diagram of a display example when information corresponding to biological signals transmitted from a plurality of patient monitoring apparatuses are displayed in a single screen by the process of the flowchart of FIG. 10.
Figure 11B:
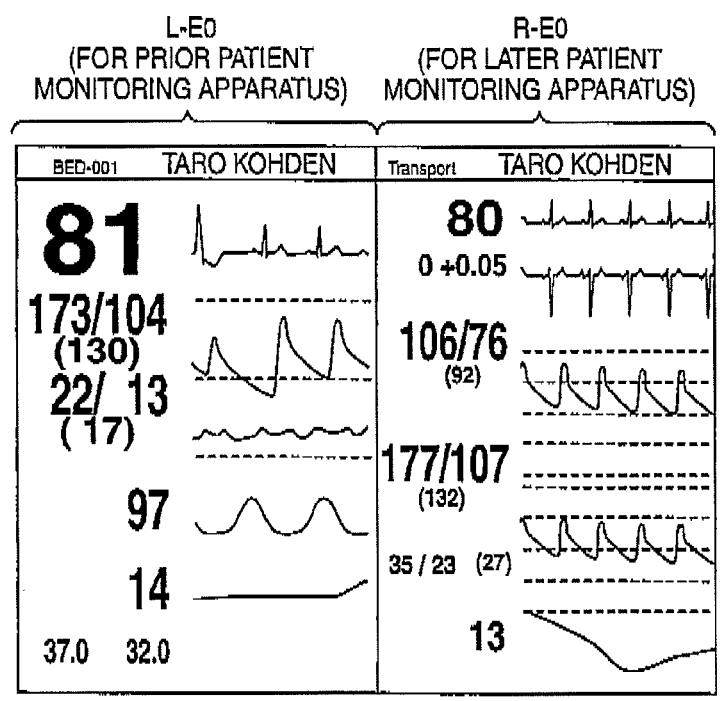
FIG. 11B is a photograph serving as a diagram of a display example when information corresponding to biological signals transmitted from a plurality of patient monitoring apparatuses are displayed in a single screen by the process of the flowchart of FIG. 10.
Figure 11C:
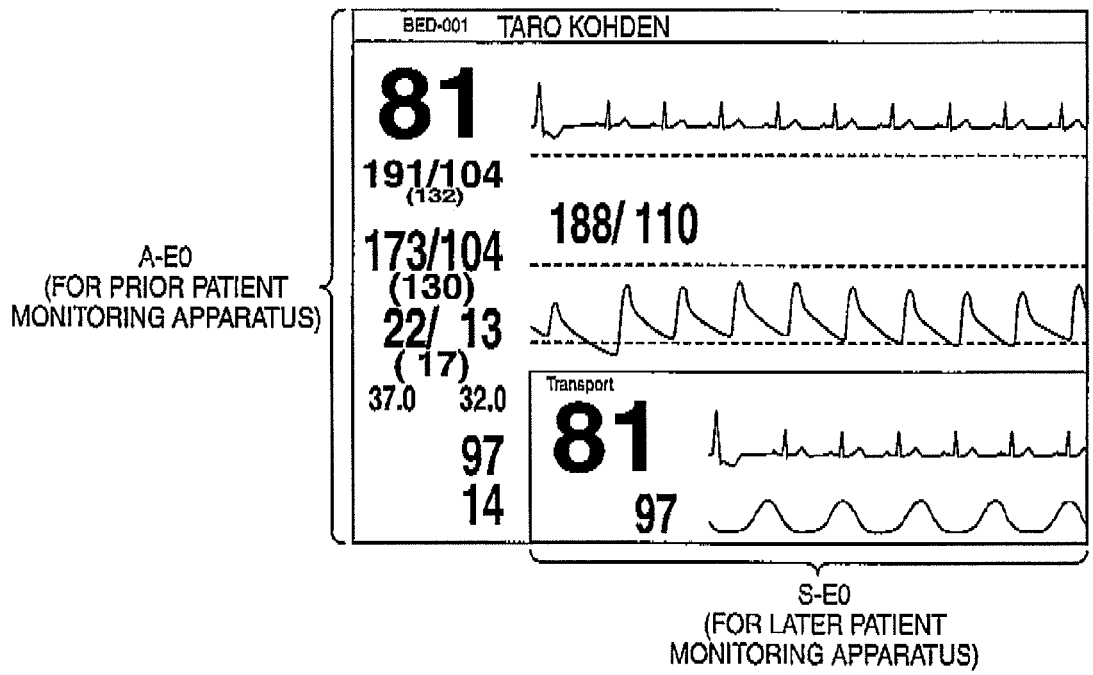
FIG. 11C is a photograph serving as a diagram of a display example when information corresponding to biological signals transmitted from a plurality of patient monitoring apparatuses are displayed in a single screen by the process of the flowchart of FIG. 10.

In this case, the information from patient monitoring apparatuses (prior patient monitoring apparatuses) that had been displayed up until then is displayed in a basically larger area at a side that normally receives attention (for example, a left side in a case where dual partition into left and right areas is performed or an upper side in a case where dual partition into upper and lower areas is performed). Examples of dually divided displays in cases where such a display format determination algorithm is set are shown in FIGS. 11A, 11B, and 11C. FIG. 11A shows an example of dual partition into upper and lower areas with an upper screen area U-E0 being larger than a lower screen area D-E0, the information from the prior patient monitoring apparatus being displayed in the upper screen area U-E0, and information from a later patient monitoring apparatus being displayed in the lower screen area D-E0. FIG. 11B shows an example of uniform dual partition into left and right areas, with the information from the prior patient monitoring apparatus being displayed in a left screen area L-E0, and information from the later patient monitoring apparatus being displayed in a right screen area R-E0. FIG. 11C shows an example where an area A-E0, taking up substantially an entire screen, is designated as an area for displaying the information from the prior patient monitoring apparatus and the information from the later patient monitoring apparatus is displayed in a small area S-E0.

Figure 11D:
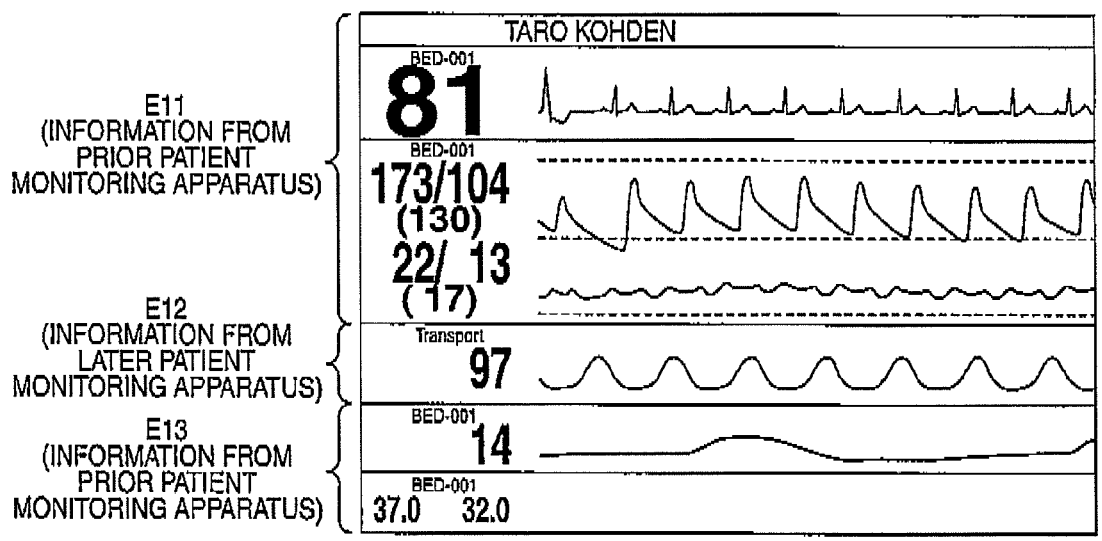
FIG. 11D is a photograph serving as a diagram of a display example when information corresponding to biological signals transmitted from a plurality of patient monitoring apparatuses are displayed in a single screen by the process of the flowchart of FIG. 10.

Furthermore, as an algorithm for determining the display format, a priority order is specified for the parameters, and biological information of a parameter of high priority is displayed in the basically larger area at the side that normally receives attention (for example, the left side in the case where dual partition into the left and right areas is performed or the upper side in the case where dual partition into the upper and lower areas is performed). FIG. 11D shows a display example corresponding to three parameters, with the biological information of predetermined parameters being displayed in areas E11, E12, and E13, respectively. In this case, the information from the prior patient monitoring apparatus may be displayed in the areas E11 and E13 and the information from the later patient monitoring apparatus may be displayed the area E12. When the patient unique ID of the patient monitoring apparatus being displayed is changed or when the patient monitoring apparatus transits from a measuring state to a non-measuring state, the display corresponding to the patient monitoring apparatus is interrupted and in step S33, the display format of the biological information arriving at that point is determined.

Because display is performed in the above-described manner, even in the case where a patient monitoring apparatus is exchanged or replaced, seamless monitoring of the biological information corresponding to the biological signals related to a desired patient is enabled, and even when a patient monitoring apparatus is added temporarily, the biological information can be monitored without interruption.

Figure 12A:
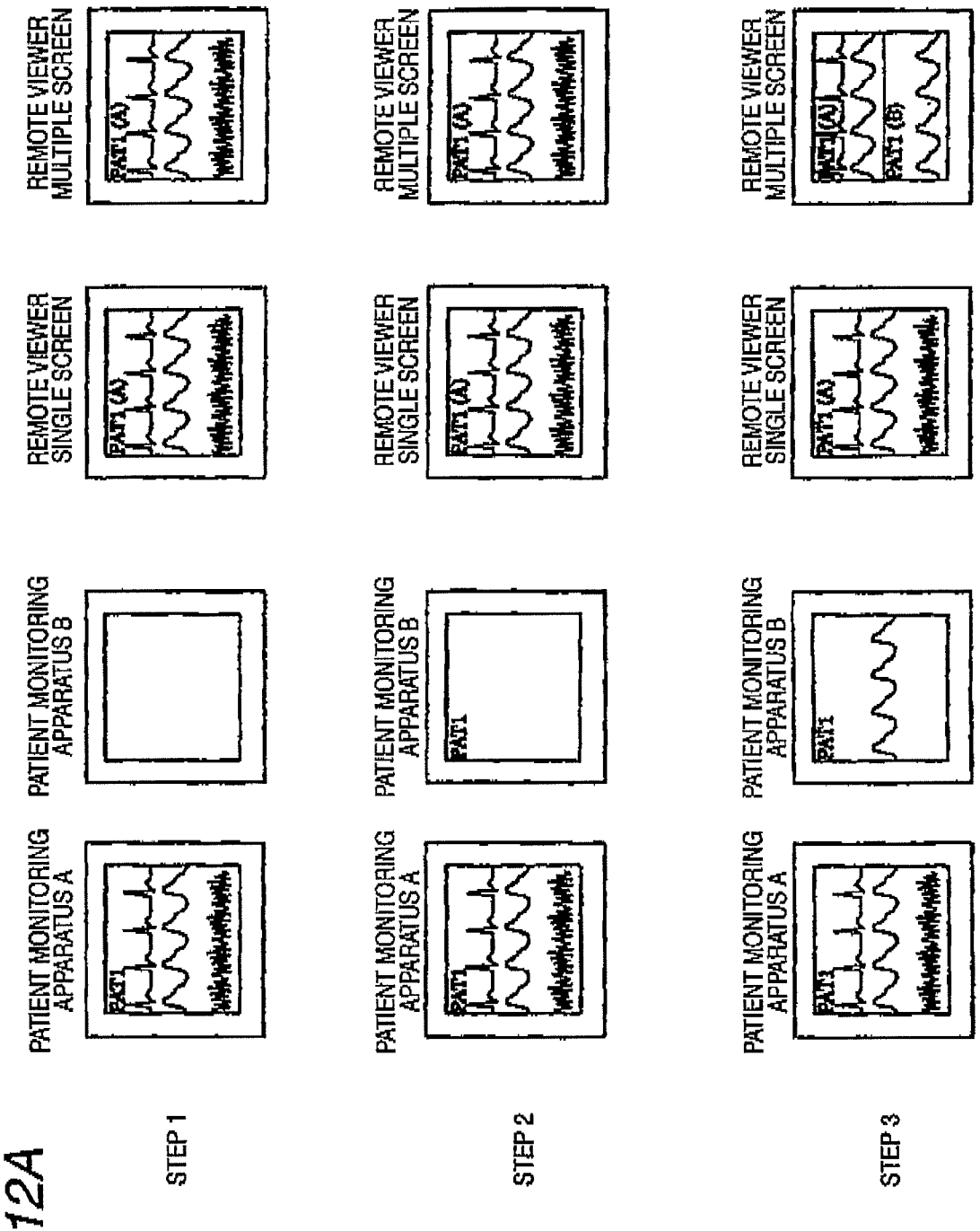
FIG. 12A is a diagram of a first half of examples of variation with time of displays in respective monitors when the operation according to the patient monitoring apparatus switching display function of the central monitor, constituting the monitoring network system according to the first embodiment of the present invention, is performed.

FIGS. 12A and 12B show examples of variation of display modes by the single screen function and the multiple screen function. In FIGS. 12A and 12B, a display screen of the patient monitoring apparatus A, collecting the biological signals earlier, a display screen of the patient monitoring apparatus B, collecting the biological signals later, a single screen area of the central monitor 20 set to the single screen function, and a single screen area of the central monitor 20 set to the multiple screen function are arranged in a row. Each biological information item is displayed as a waveform. An ECG (electrocardiogram) waveform is set as an important parameter. As the display format set in step S33 of the multiple screen function, the entire screen area is sectioned and display according to patient monitoring apparatus is performed in an order starting from the patient monitoring apparatus with which measurements are being performed earlier.

In step 1, which is an initial state (default), an image on the display screen of the patient monitoring apparatus A, an image in the screen area of the central monitor 20 set to the single screen function, and an image in the screen area of the central monitor 20 set to the multiple screen function are matched, and a display is not performed on the display screen of the patient monitoring apparatus B. Step 2 shows a state where, in the patient monitoring apparatus B, although a patient unique ID is taken in via the scanner 45, etc., the acquisition of biological signals is not yet started. In step 2, the same screen displays as those of the initial state are performed.

Step 3 shows a state where intake of the biological signals is started at the patient monitoring apparatuses A and B. In step S3, whereas sectioning into the predetermined display sections is performed and the waveforms corresponding to the biological signals acquired at the patient monitoring apparatuses A and B are displayed in the display screen of the central monitor 20 that is set to the multiple screen function, because the biological signals of the ECG waveform, which is the important parameter, continues to be acquired from the patient monitoring apparatus A, the same image as the image on the display screen of the patient monitoring apparatus A is displayed in the display screen of the central monitor 20 that is set to the single screen function.

Step 4 shows a state where the acquisition of the biological signals of the ECG waveform, which is the important parameter, is started at the patient monitoring apparatus B. In step 4, because the biological signals of the ECG waveform, which is the important parameter, continues to be acquired from the patient monitoring apparatus A, the same image as the image on the display screen of the patient monitoring apparatus A is displayed in the display screen of the central monitor 20 set to the single screen function. In the display screen of the central monitor 20 set to the multiple screen function, sectioning into the predetermined display sections is performed and the waveforms corresponding to the biological signals collected at the patient monitoring apparatuses A and B are displayed.

Step 5 shows a state where the intake of the biological signals of the ECG waveform, which is the important parameter, from the prior patient monitoring apparatus A is stopped. In step 5, the same image as the image in the display screen of the later patient monitoring apparatus B is displayed in the display screen of the central monitor 20 set to the single screen function. In the display screen of the central monitor 20 set to the multiple screen function, sectioning into the predetermined display sections is performed and the waveforms corresponding to the biological signals collected at the patient monitoring apparatuses A and B are displayed.

Step 6 shows a state where the acquisition of all biological signals, including that of the ECG waveform, which is the important parameter, from the prior patient monitoring apparatus A is stopped. In step 6, the same image as the image in the display screen of the later patient monitoring apparatus B is displayed in the display screen of the central monitor 20 set to the single screen function. In the display screen of the central monitor 20 set to the multiple screen function, because the arrival of the biological signals from the prior patient monitoring apparatus A is stopped, the process of sectioning into the predetermined display sections is stopped and the waveforms corresponding to the biological signals acquired at the patient monitoring apparatus B are displayed in the entire screen area.

Second Embodiment

Figure 13:
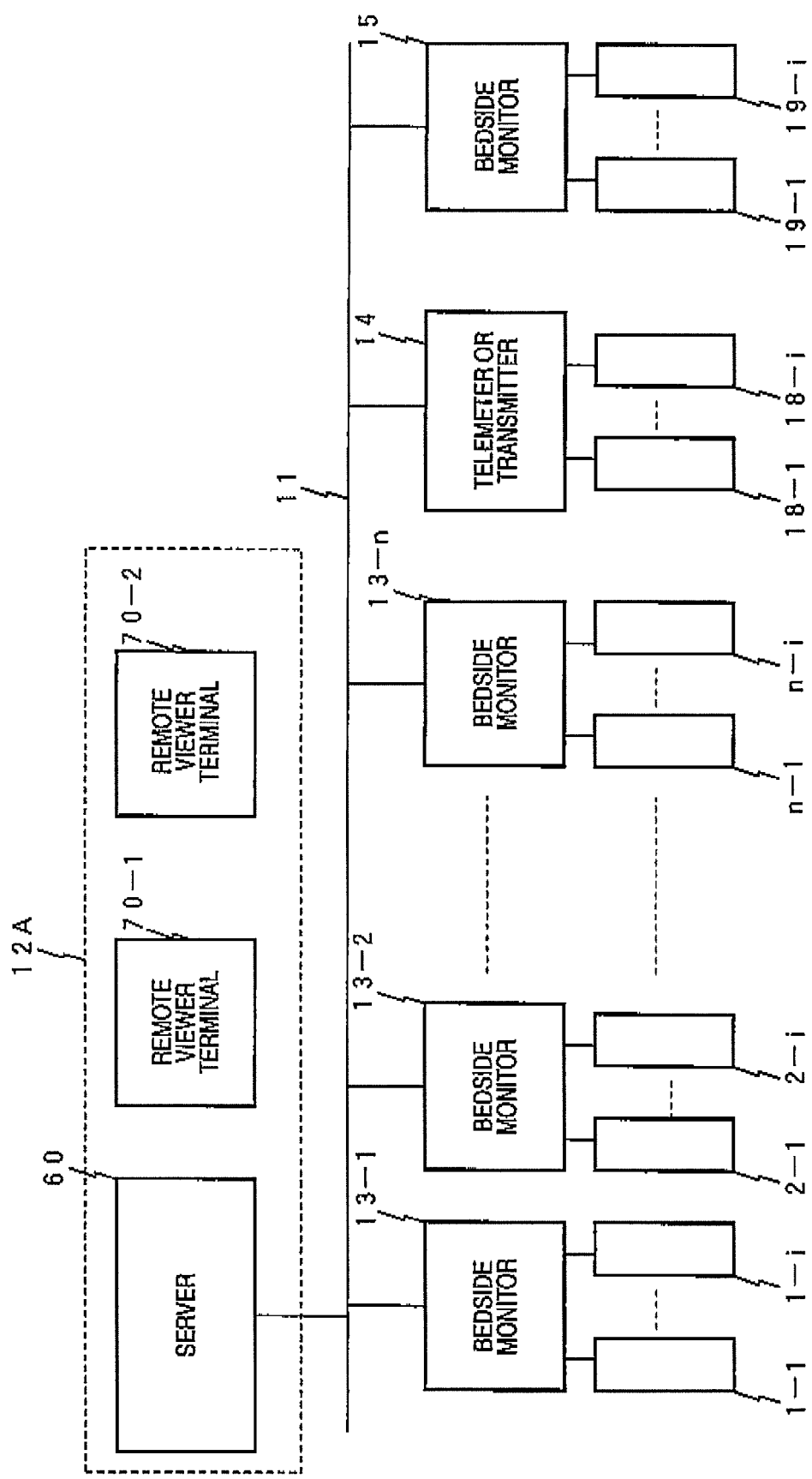
FIG. 13 is a block diagram of a monitoring network system according to the first embodiment of the present invention.

FIG. 13 shows a monitoring network system according to a second embodiment, with which a remote monitoring apparatus 12A is constituted of a server 60 and the remote viewer terminals 70-1 and 70-2. The number of remote viewer terminals shown here is merely an example. Besides the configuration of the remote monitoring apparatus 12, the second embodiment does not differ from the first embodiment.

Figure 14:
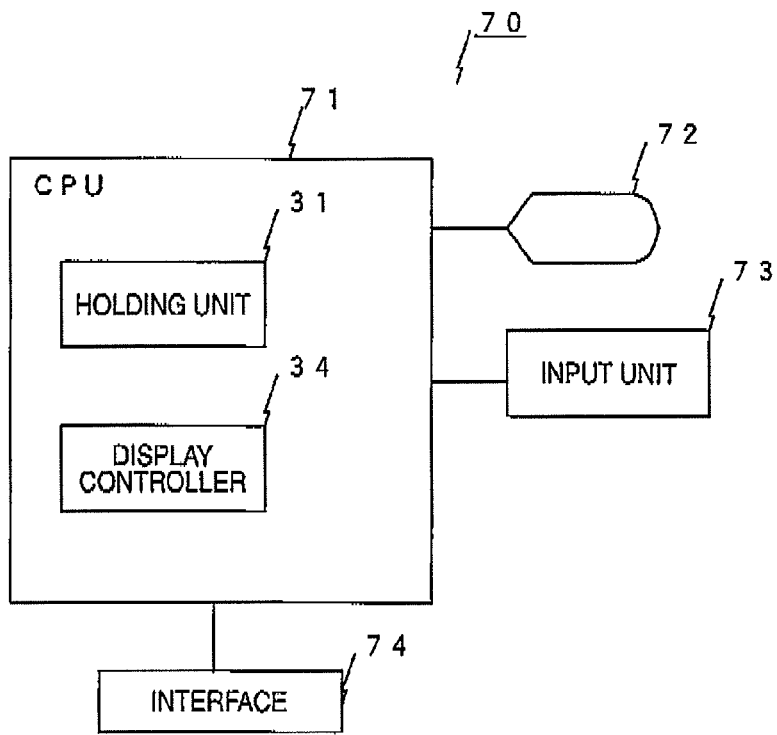
FIG. 14 is a block diagram of a remote viewer terminal, constituting the monitoring network system according to a second embodiment of the present invention.

As shown in FIG. 14, each of the remote viewer terminals 70-1 and 70-2 is mainly constituted of the CPU 71 and includes a display unit 72, constituted of an LCD, etc., a keyboard, mouse device, or other input unit 73, and an interface 74, connected to the network 11, as main components. The CPU 71 includes the holding unit 31 and the display controller 34. The holding unit 31 and the display controller 34 are as has been described already. A screen area of the display unit 72 may be sectioned as shown in FIG. 4 or may be a single, non-sectioned screen area.

Figure 15:
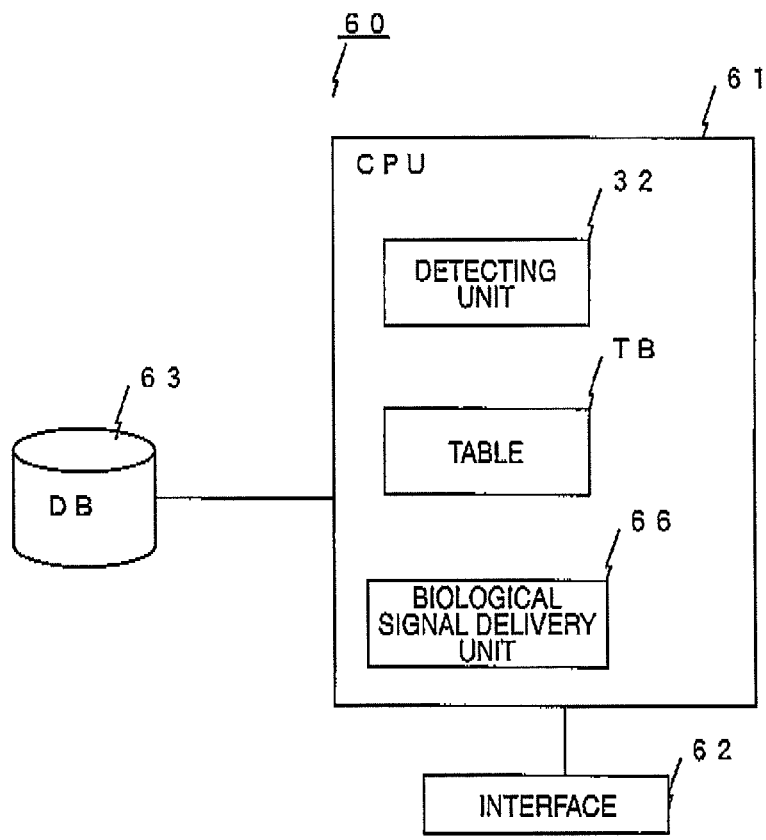
FIG. 15 is a block diagram of a server, constituting the monitoring network system according to the second embodiment of the present invention.
Figures 16, 17:
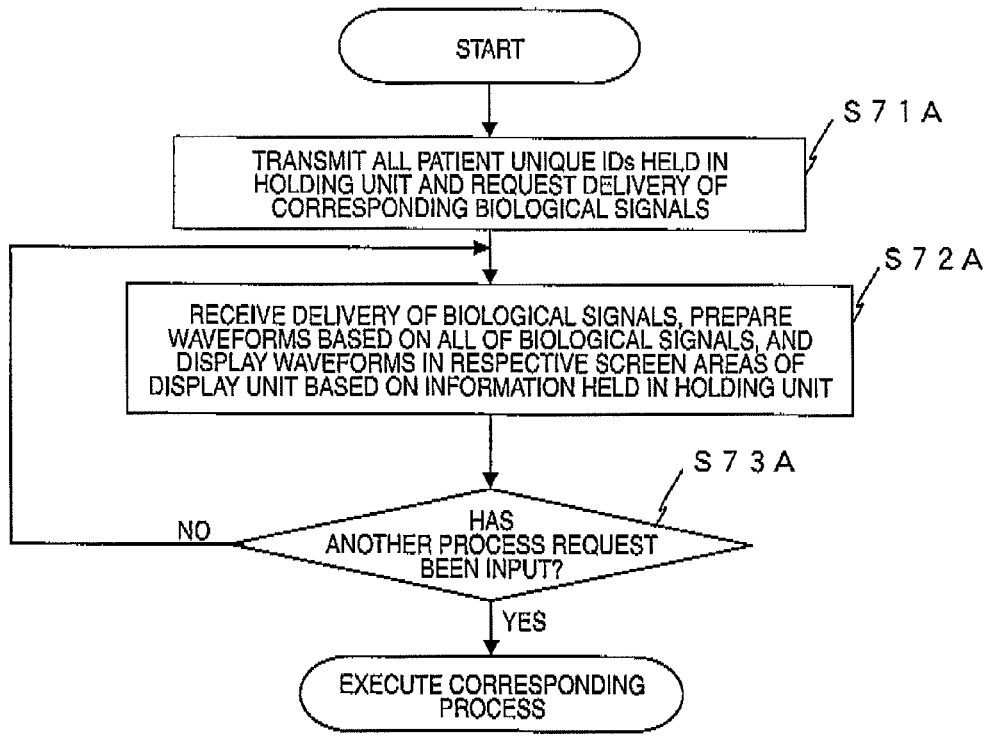
FIG. 16 is a diagram of an example of information stored in a table included in the server, constituting the monitoring network system according to the second embodiment of the present invention.
FIG. 17 is a flowchart for describing an operation of the remote viewer terminal, constituting the monitoring network system according to the second embodiment of the present invention, and is a flowchart of a process in a case where biological signals are transmitted via the server.

As shown in FIG. 15, the server 60 is mainly constituted of a CPU 61 and includes an interface 62, connected to the network 11, and the same database DB as that shown in FIG. 5 as main components. The CPU 61 includes the same detecting unit 32 included in the CPU 21 of FIG. 1. The CPU 61 includes a table TB having contents such as shown in FIG. 16 and storing identification information of patient monitoring apparatuses, acquiring biological signals associated with patient unique IDs obtained from the detecting unit 32. The table TB is renewed by the detecting unit 32.

The CPU 61 furthermore includes a biological signal delivery unit 66 that collects the biological signals from the respective bedside monitors 13-1 to 13-n, the telemeter OR transmitter 14, and the bedside monitor 15 and transmits desired biological signals according to requests from the remote viewer terminals 70-1 and 70-2. The server 60 may transmit the identification information of the desired patient monitoring apparatuses to the remote viewer terminals 70-1 and 70-2, and the remote viewer terminals 70-1 and 70-2 may receive the biological signals from the patient monitoring apparatuses corresponding to the received identification information. As with DB 26, a DB 63 holds the patient identification information, the patient unique IDs for specifying patients, and the association of the patient unique IDs and the patient identification information as shown in FIG. 5. The CPU 61 has the function of using the DB 63 to search held information based on the input patient identification information and thereby specifying the patient unique ID.

With the monitoring network system configured as described above, upon startup, the server 60 in the remote monitoring apparatus 12A collects the patient unique IDs held in the patient unique ID holding units 51 of the bedside monitors 13-1 to 13-n, the telemeter OR transmitter 14, and the bedside monitor 15.

The patient unique IDs acquired and the identification information of the patient monitoring apparatuses from which the patient unique IDs could be acquired are associated and stored in the table TB. If notification of a predetermined state, including the non acquirable state, is made from any of the blood pressure sensors, electrocardiogram sensors, and other acquisition units 1-1 to 1-i, 2-1 to 2-i, ..., n-1 to n-i, and 19-1 to 19-i, the same notification is transmitted to the remote monitoring apparatus 12A, which is the target of transmission of the biological signals.

Figure 18:
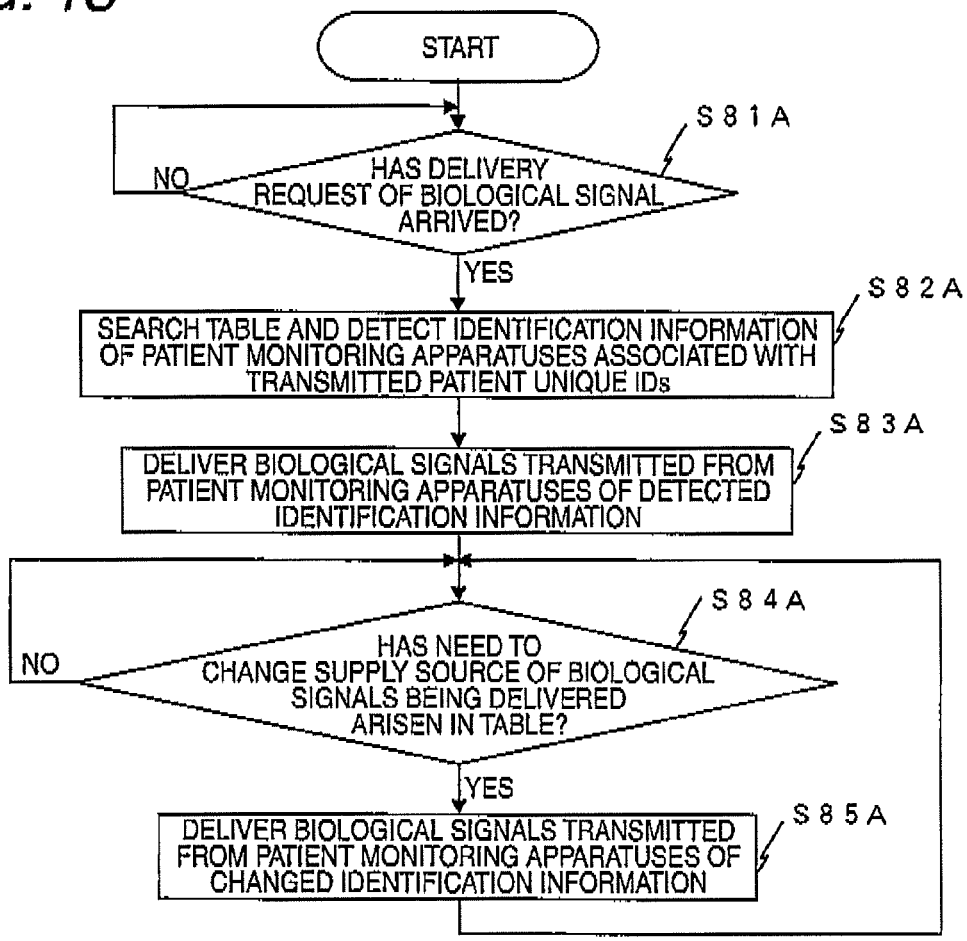
FIG. 18 is a flowchart for describing an operation of the server, constituting the monitoring network system according to the second embodiment of the present invention, and is a flowchart of a process in a case where biological signals are transmitted via the server.
Figure 19:
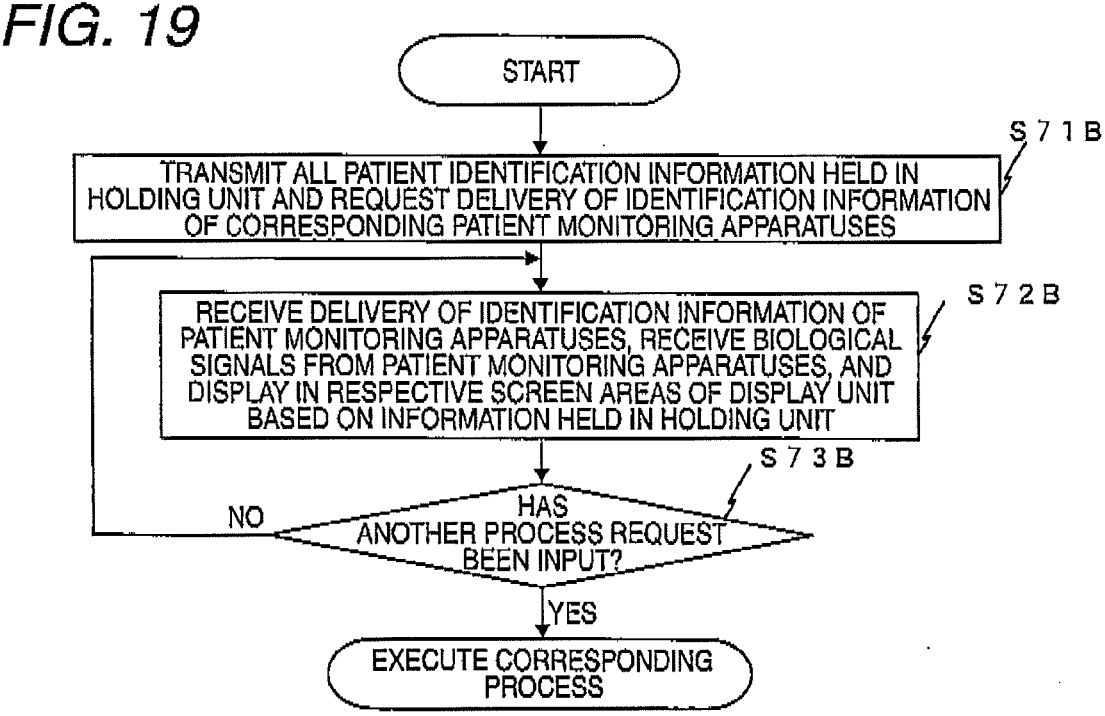
FIG. 19 is a flowchart for describing an operation of the remote viewer terminal, constituting the monitoring network system according to the second embodiment of the present invention, and is a flowchart of a process in a case where biological signals are transmitted but not via the server.
Figure 20:
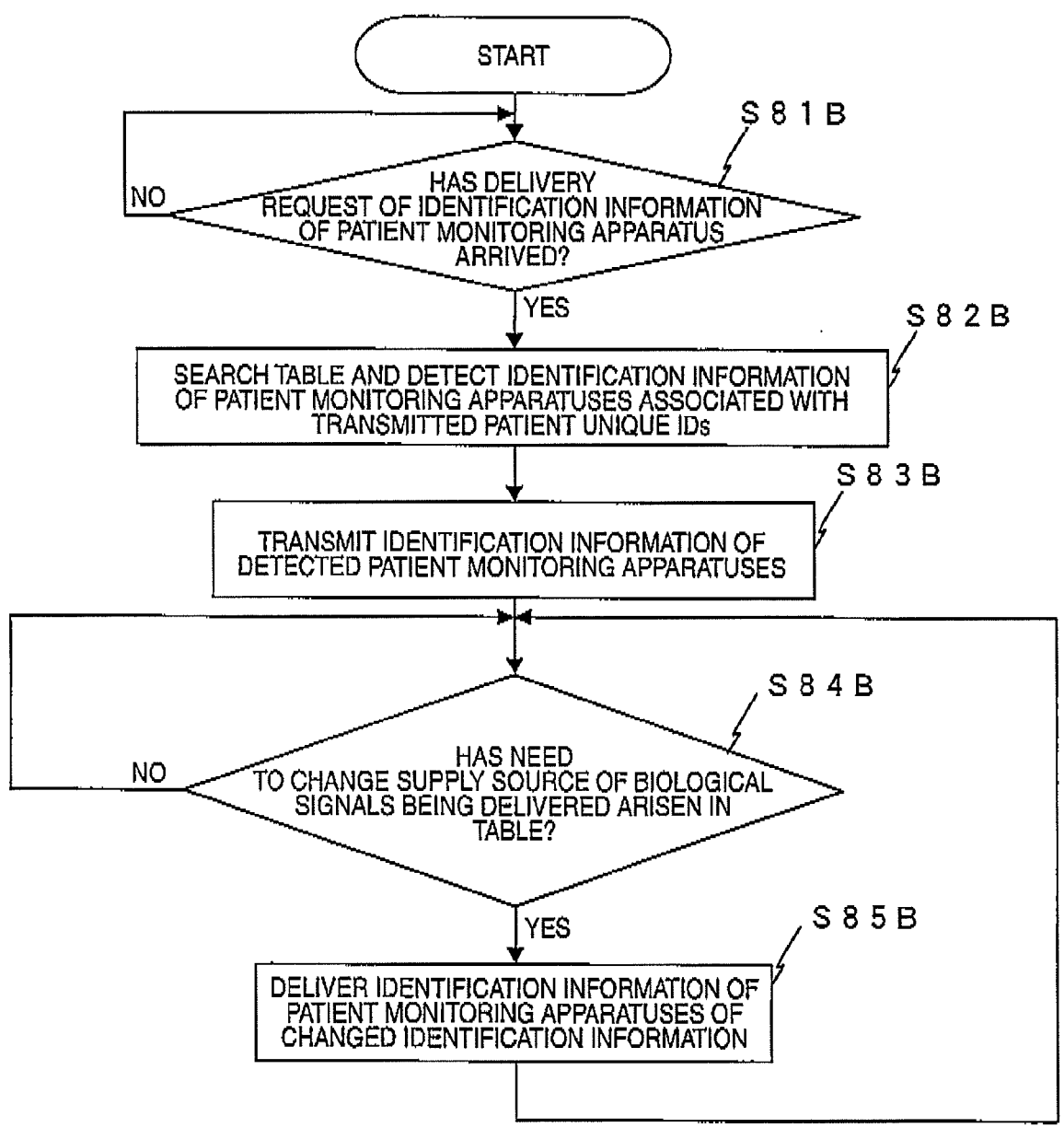
FIG. 20 is a flowchart for describing an operation of the server, constituting the monitoring network system according to the second embodiment of the present invention, and is a flowchart of a process in a case where biological signals are transmitted but not via the server.

In regard to the above, because when the instruction to perform multi monitoring display of a plurality of patients is made to the remote viewer terminals 70-1 and 70-2, the CPU 71 performs an operation using a program corresponding to a flowchart 4 shown in FIG. 17 or 19 to realize the respective units of FIG. 14, and accordingly the CPU 61 of the server 60 performs an operation using a program corresponding to a flowchart shown in FIG. 18 or 20, the operations shall now be described based on these drawings. Here, FIGS. 17 and 18 show the operations in a case where biological signals are transmitted via the server 60. FIGS. 19 and 20 show the operations in a case where biological signals are not transmitted via the server 60. The operations in a case where biological signals are transmitted via the server 60 shall now be described with reference to FIGS. 17 and 18. The CPU 71 transmits all patient unique IDs, held in the holding unit 31, to the server 60, and transmits, to the patient monitoring apparatuses, a request to transmit the biological signals of the patients corresponding to the patient unique IDs (S71A).

With respect to the request from the CPU 71, the CPU 61 of the server 60 monitors an arrival of the request to transmit the biological signals (S81A) as shown in the flowchart of FIG. 18, and in accordance with the arrival of the request, searches the table TB and detects the identification information of all of the corresponding patient monitoring apparatuses (S82A). The CPU 61 of the server 60 furthermore converts the biological signals, transmitted from all patient monitoring apparatuses corresponding to the identification information of the patient monitoring apparatuses detected in step S82A, for transmission through the network 11 and delivers the signals to remote viewer terminals (70-1 and 70-2).

The CPU 71 of each of the remote viewer terminals (70-1 and 70-2) receives the delivered biological signals and displays the biological signals at the corresponding screen areas based on the screen area information associated with the patient unique ID held in the holding unit 31 (S72A), detects whether or not another process request has been input (S73A), and proceeds to the corresponding process if another process request has been input or continues with the process of step S72A it another process request has not been input.

In continuation from step S83A, the CPU 61 of the server 60 searches the table TB, checks whether or not a change has been made in the identification information of the patient monitoring apparatuses corresponding to all of the patient unique IDs transmitted from the CPUs 71 of the remote viewer terminals (70-1 and 70-2) (S84A), and if a change is detected, delivers the biological signals transmitted from the patient monitoring apparatus after the change in place of the biological signals transmitted from the patient monitoring apparatus before the change corresponding to the patient unique ID (S85A). In step S84A, in regard to the patient monitoring apparatuses corresponding to the patient identification information other than those for which a change is detected, the transmission of the biological signals from these patient monitoring apparatuses is continued without change.

The operations in a case where biological signals are not transmitted via the server 60 shall now be described with reference to FIGS. 19 and 20. The CPU 71 transmits all patient unique IDs, held in the holding unit 31, to the server 60, and transmits a request for delivery of biological signals by the patient monitoring apparatuses having the identification information associated with the patient unique IDs (S71B).

With respect to the request from the CPU 71, the CPU 61 of the server 60 monitors an arrival of information requesting the identification information of the patient monitoring apparatuses (S81B) as shown in the flowchart of FIG. 20, and in accordance with the arrival of the request, searches the table TB and detects the identification information of all of the corresponding patient monitoring apparatuses (S82B). The CPU 61 of the server 60 furthermore converts the identification information of the patient monitoring apparatuses detected in step S82B for transmission through the network 11 and delivers the information to the remote viewer terminals (70-1 and 70-2).

Based on the delivered identification information of the patient monitoring apparatus, the CPU 71 performs a process of receiving the biological signals from the corresponding patient monitoring apparatuses, performs display in the screen area associated with the patient unique ID held in the holding unit 31 (S72B), detects whether or not another process request has been input (S73B), and proceeds onto the corresponding process if another process request has been input or continues with the process of step S72B if another process request has not been input.

In continuation from step S83B, the CPU 61 of the server 60 searches the table TB, checks whether or not a change has been made in the identification information of the patient monitoring apparatuses corresponding to all of the patient unique IDs transmitted from the CPUs 71 of the remote viewer terminals (70-1 and 70-2) (S84B), and if a change is detected, delivers the patient identification information associated with the patient monitoring apparatus after the change in place of the patient identification information associated with the patient monitoring apparatus before the change corresponding to the patient unique ID (S85B). In step S84B, in cases besides the case where a change is detected, the patient identification information associated with the patient monitoring apparatus after change is not delivered, and the patient identification information associated with the already transmitting patient monitoring apparatuses is maintained without change.

In performing display on the display unit 72, the monitor name and the monitor location (hospital room number and patient bed number), which are information specifying the patient monitoring apparatus acquiring the biological signal corresponding to each displayed waveform, the control department or other identification information specifying the patient monitoring apparatus, the patient name held in the holding unit 31, etc., are displayed in association with the waveform. Because the identification information specifying the patient monitoring apparatus acquiring the biological signal corresponding to each waveform is transmitted along with the biological signal from the CPU 61 of the server 60, this information is used. Waveforms are thus displayed on the display unit 72 as shown for example in FIG. 8. Here, even when the patient name (Taro Kohden) is transferred from the patient monitoring apparatus of the monitor name (ICU0001) to the patient monitoring apparatus of the monitor name (ICU0011) and measurements are made, waveforms based on the biological signals corresponding to the patient name (Taro Kohden) are displayed in the section E1. Because the patient monitoring apparatuses are switched in this case, the patient name (Taro Kohden) and the new monitor name (for example, ICU0011) are displayed additionally in the section E1.

<Patient Monitoring Apparatus Switching Display Function (Display Function by Changeover of Patient Monitoring Apparatus)>

The remote monitoring apparatus 12 also has the patient monitoring apparatus switching display function that was described with the first embodiment.

Figure 21:
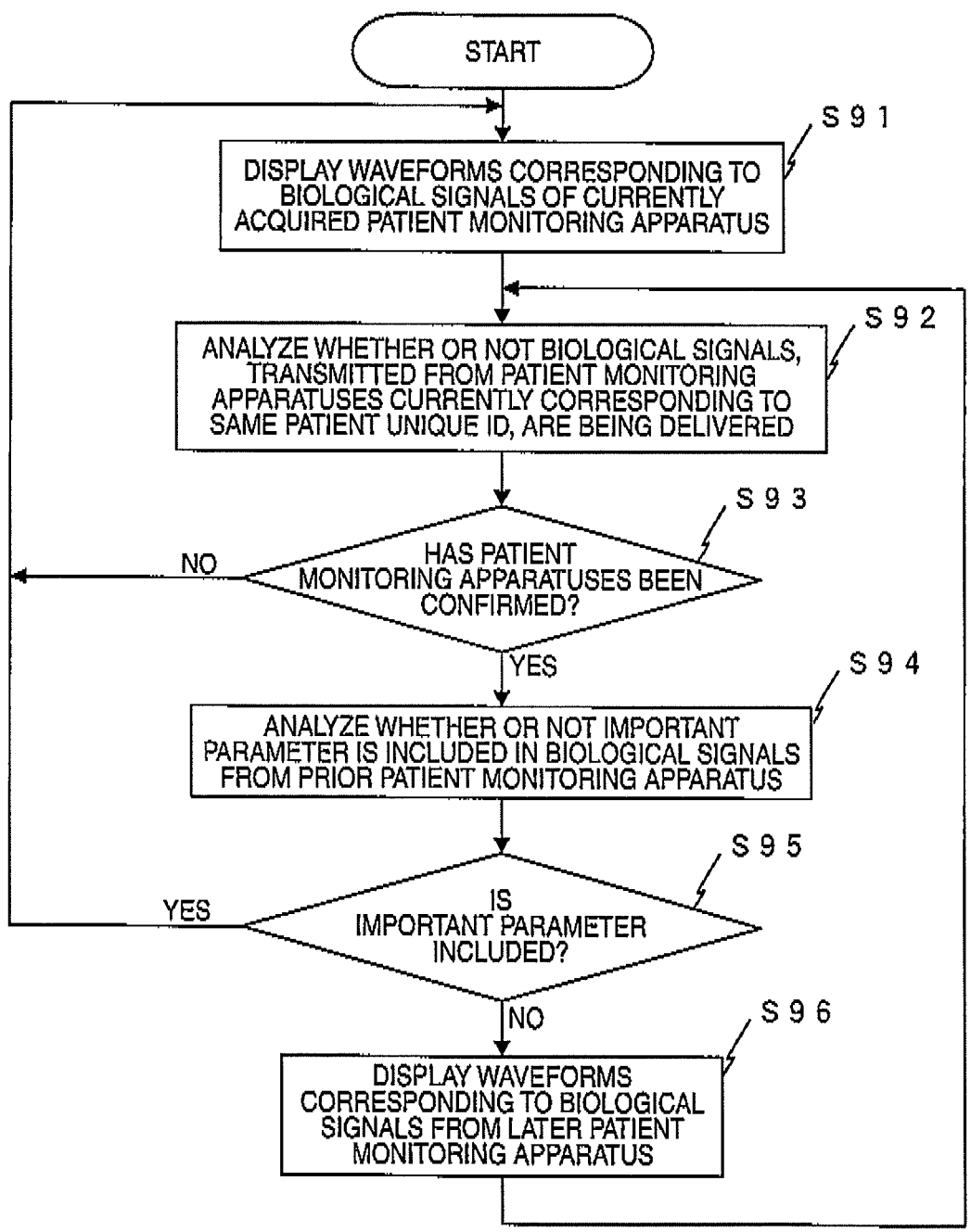
FIG. 21 is a flowchart for describing an operation according to the patient monitoring apparatus switching display function of the server, constituting the monitoring network system according to the second embodiment of the present invention.

FIG. 21 is a flowchart of the process by the single screen function and an operation according to the single screen function shall now be described based on this flowchart. Waveform display corresponding to the currently acquired biological signals from the patient monitoring apparatuses is performed (S91), whether or not a plurality of biological signals obtained from a plurality of patient monitoring apparatuses corresponding to the same patient unique ID are being delivered is analyzed (S92), and whether or not multiple delivery is being performed is determined (S93). If multiple delivery is not being performed, step S91 is returned to and the process there is performed, and if multiple delivery is being performed, it is analyzed whether or not a state, where an important parameter, set in advance, is included in the biological signals from a prior patient monitoring apparatus, is maintained (S94) and it is detected whether or not an important parameter is included (S95).

If in step S95, continuation of arrival of the important parameter is confirmed, step S91 is returned to and the process there is performed, and if in step S95, continuation of arrival of the important parameter cannot be confirmed, waveform display corresponding to the biological signals from the later patient monitoring apparatus is performed (S96) and then step S92 is returned to and the process there is performed. Because display is performed in this manner, even in a case where a patient monitoring apparatus is exchanged or replaced, seamless monitoring of the waveforms corresponding to the biological signals related to a desired patient is enabled.

Figure 22:
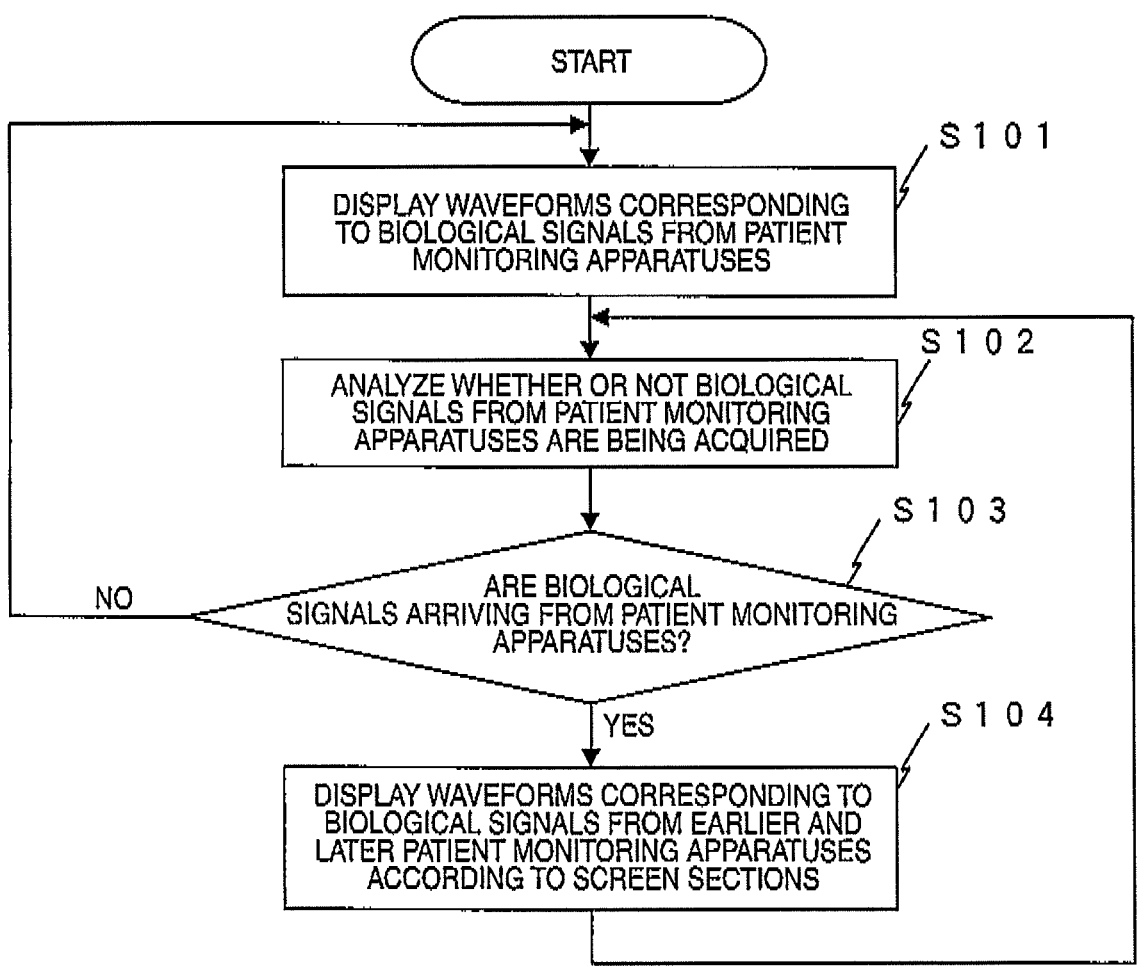
FIG. 22 is a flowchart for describing an operation according to the patient monitoring apparatus switching display function of the server, constituting the monitoring network system according to the second embodiment of the present invention.

FIG. 22 is a flowchart of the process by the multiple screen function and an operation according to the multiple screen function shall now be described based on this flowchart. Waveform display corresponding to the currently acquired biological signals from the patient monitoring apparatuses is performed (S101), the arrival of biological signals acquired from a plurality of patient monitoring apparatuses is analyzed (S102), and whether or not biological signals of the same patient are arriving from a plurality of patient monitoring apparatuses is determined (S103). If in step S103, the arrival of biological signals is not confirmed, step S101 is returned to and the process there is performed, and if the arrival of biological signals from a plurality of patient monitoring apparatuses is confirmed, display is performed upon sectioning a single screen of the display unit 22 for the waveform displays corresponding to the biological signals from the earlier and later patient monitoring apparatuses (the biological signals transmitted from all of the patient monitoring apparatuses from which the biological signals are arriving) (S104) and then step S102 is returned to and the process there is performed.

Because display is performed as described above in the second embodiment, in a case where a patient monitoring apparatus is exchanged or replaced, transmission of signals, resulting from conversion of the biological signals from the transmission processing units 52 of the plurality of processing devices and transmitted through the network 11, is received, display is performed upon sectioning the display unit 22 into the predetermined screen areas, and seamless monitoring of the waveforms corresponding to the biological signals related to a desired patient is enabled. As in the first embodiment, the display is transited as shown in FIG. 12 by the patient monitoring apparatus switching display function (display function by changeover of patient monitoring apparatus) in the second embodiment as well.

As described above, with the present invention, because each of the patient monitoring apparatuses includes the patient unique ID holding unit, holding the patient unique ID associated with the patient identification information input into the patient monitoring apparatus, and the remote monitoring apparatus includes the holding unit, holding the screen area information of the display unit in association with the patient unique ID, the detecting unit, detecting the patient monitoring apparatus holding the same patient unique ID as the patient unique ID held in the holding unit, the receiving processing unit, receiving the biological signal from the transmission processing unit of the patient monitoring apparatus detected by the detecting unit, and the display controller, which, in displaying either or both of the biological signal and the patient identification information based on the received signal on the display unit, displays in a corresponding screen area based on the information held in the holding unit, the biological signal, measured by the patient monitoring apparatus holding the corresponding patient unique ID, is displayed in the corresponding screen area, and monitoring by the remote monitoring apparatus is enabled regardless of where a patient is and by which patient monitoring apparatus the patient is being measured.

Also with the monitoring network system according to the present invention, because each of the patient monitoring apparatuses further includes the notifying unit, detecting and notifying predetermined states, including at least the non acquirable state, and the detecting unit of the remote monitoring apparatus starts the detecting process when it receives the notification from the notifying unit, detection of the patient monitoring apparatus holding the same patient unique ID is performed when a predetermined state is detected, and even when the patient moves and it is not necessary that a medical staff perform an operation of specifying the patient monitoring apparatus measuring the patient in question and reinputting the information on the patient monitoring apparatus into the remote monitoring apparatus, the biological signals can be acquired from the patient monitoring apparatus corresponding to the patient unique ID to enable continuous monitoring without interruption.

Furthermore, when the remote monitoring apparatus is to monitor a biological signal of a desired patient, switching to the patient monitoring apparatus acquiring the biological signal of the desired patient is performed automatically and there is no need to monitor all of the patient monitoring apparatuses.

Also with the monitoring network system according to the present invention, because when the detecting unit detects a plurality of patient monitoring apparatuses acquiring biological signals corresponding to a same patient unique ID, the transmission of a signal, converted from a biological signal and transmitted through the network, is received from the transmission processing unit of a single patient monitoring apparatus among the patient monitoring apparatuses and the signal is displayed in a single area of the display unit, by making the biological signal from the predetermined single patient monitoring apparatus be displayed with priority, a display that is easy to view due to screen transitions being few is made possible even when a change of patient monitoring apparatus is performed.

Also with the monitoring network system according to the present invention, because when the detecting unit detects a plurality of patient monitoring apparatuses acquiring biological signals corresponding to a same patient unique ID, the transmission of signals, converted from biological signals and transmitted through the network, is received from the transmission processing units of two or more patient monitoring apparatus among the patient monitoring apparatuses and the biological signal or biological signals of a single or a plurality of patient monitoring apparatuses are displayed in a comprehensive manner in a single area of the display unit, by displaying the biological signals transmitted from the two or more patient monitoring apparatuses among the patient monitoring apparatuses, a display that accommodates the biological signals measured by patient monitoring apparatuses that are added to the patient is enabled.

Furthermore, by displaying, in the corresponding screen area, a biological signal of a patient and the information concerning the patient monitoring apparatus acquiring the biological signal of the patient, a monitoring staff can readily check the state of the patient and rapidly prepare for treatment of the patient.

What is claimed is:

1. A monitoring network system, comprising:
a plurality of monitoring apparatuses; and
a remote monitoring apparatus, connected to the plurality of monitoring apparatuses via network,
wherein at least one of the plurality of monitoring apparatuses is configured to acquire biological signals from a patient and includes:
a first holder, configured to hold a first ID and first information for identifying the patient which is associated with the first ID, wherein the first ID is a unique patient identifier; and
a transmitter, configured to transmit the biological signal and the first ID to the remote monitoring apparatus, and wherein the remote monitoring apparatus includes:
a second holder, configured to hold a second ID and association information for associating a screen area in a display with the second ID, wherein the second ID is a unique patient identifier;
a detector, configured to detect the at least one of the plurality of monitoring apparatuses whose the first holder holds the first ID, when the first ID is identical with the second ID;
a receiver, configured to receive the biological signal, the first ID, and the first information from the at least one of the plurality of monitoring apparatuses detected by the detector; and
a display controller, configured to display the at least one of the biological signal and the first information on the screen area in the display based on the association information.

2. The monitoring network system according to claim 1, wherein the remote monitoring apparatus includes:
a storage, configured to store the biological signals from the at least one of the plurality of monitoring apparatuses each of which holds the first ID; and
a joiner, configured to join the stored biological signals in time series, and
wherein the display controller displays the joined biological signals on the screen area in the display based on the association information.

3. The monitoring network system according to claim 1, wherein
the remote monitoring apparatus includes a central monitor including a computer.

4. The monitoring network system according to claim 1, wherein
the remote monitoring apparatus includes:
at least one server; and
a remote viewer terminal, and
the at least one server includes:
an identifier, configured to specify the first ID based on the first information; and
the detector.

5. The monitoring network system according to claim 1, wherein
each of the plurality of monitoring apparatus includes a notifier, configured to transmit, to the remote monitoring apparatus, a notification to notify a state in which the each of the plurality of monitoring apparatus is disable to acquire the biological signal, and
after receiving the notification from the at least one of the plurality of monitoring apparatuses whose the first holder holds the first ID, the remote monitoring apparatus starts to perform a detection operation for detecting the at least one of the plurality of monitoring apparatuses whose the first holder holds the first ID.

6. The monitoring network system according to claim 1, wherein
when the receiver receives the biological signals from the at least one of the plurality of monitoring apparatuses each of which holds the first ID, the display controller displays only one of the received biological signals.

7. The monitoring network system according to claim 1, wherein
when the receiver receives the biological signals from the at least one of the plurality of monitoring apparatuses each of which holds the first ID, the display controller displays at least one of the biological signals.

8. The monitoring network system according to claim 1, wherein
the display controller displays second information for identifying the at least one of the plurality of monitoring apparatuses from which the receiver receives the biological signal, together with the at least one of the biological signal and the first information.

9. A monitoring network system, comprising:
a plurality of monitoring apparatuses; and
a remote monitoring apparatus, connected to the plurality of monitoring apparatuses via network,
wherein at least a first monitoring apparatus of the plurality of monitoring apparatuses is configured to acquire biological signals from a patient and includes:
a first holder, configured to hold a first ID and first information for identifying the patient which is associated with the first ID, wherein the first ID is a unique patient identifier; and
a transmitter, configured to transmit a first biological signal and the first ID to the remote monitoring apparatus, and
wherein the remote monitoring apparatus includes:
a second holder, configured to hold a second ID and association information for associating a screen area in a display with the second ID, wherein the second ID is a unique patient identifier;
a receiver, configured to receive a plurality of biological signals and a information from the plurality of monitoring apparatuses including the first biological signal and the first information from the first monitoring apparatus of the plurality of monitoring apparatuses;
a detector, configured to detect the at least one of the plurality of monitoring apparatuses whose the first holder holds the first ID, and determine, based on whether the first ID is identical with the second ID, which of the biological signals is the first biological signal received from the first monitoring apparatus and what information is the first information received from the first monitoring apparatus;
and
a display controller, configured to display at least one of the first biological signal and the first information on the screen area in the display based on the association information when the detector determines which of the biological signals is the first biological signal received from the first monitoring apparatus and what information is the first information received from the first monitoring apparatus.

10. The monitoring network system according to claim 9, wherein the remote monitoring apparatus includes:
a storage, configured to store the biological signals from the at least a first monitoring apparatus of the plurality of monitoring apparatuses which each holds the first ID; and
a joiner, configured to join the stored biological signals in time series, and
wherein the display controller displays the joined biological signals on the screen area in the display based on the association information.

11. The monitoring network system according to claim 9, wherein
the remote monitoring apparatus includes a central monitor including a computer.

12. The monitoring network system according to claim 9, wherein
the remote monitoring apparatus includes:
at least one server; and
a remote viewer terminal, and
the at least one server includes:

an identifier, configured to specify the first ID based on the first information; and the detector.

13. The monitoring network system according to claim 9, wherein each of the plurality of monitoring apparatus includes a notifier, configured to transmit, to the remote monitoring apparatus, a notification to notify a state in which the each of the plurality of monitoring apparatus is unable to acquire the biological signal, and after receiving the notification from the at least a first monitoring apparatus of the plurality of monitoring apparatuses whose the first holder holds the first ID, the remote monitoring apparatus starts to perform a detection operation for detecting which of the plurality of monitoring apparatuses has a first holder that holds the first ID.

14. The monitoring network system according to claim 9, wherein when the receiver receives the biological signals from a plurality of monitoring apparatuses which each holds the first ID, the display controller displays only one of the received biological signals.

15. The monitoring network system according to claim 9, wherein when the receiver receives the biological signals from a plurality of monitoring apparatuses which each holds the first ID, the display controller displays at least one of the biological signals.

16. The monitoring network system according to claim 9, wherein the display controller displays second information for identifying the at least one first monitoring apparatus of the plurality of monitoring apparatuses from which the receiver receives the biological signal, together with the at least one of the biological signal and the first information.

17. A monitoring network system, comprising:

a plurality of monitoring apparatuses; and a remote monitoring apparatus, connected to the plurality of monitoring apparatuses via network, wherein a first monitoring apparatus of the plurality of monitoring apparatuses is configured to acquire biological signals from a patient and includes:

a first holder, configured to hold a first ID and first information for identifying the patient which is associated with the first ID, wherein the first ID is a unique patient identifier;

a transmitter, configured to transmit the first biological signal and the first ID to the remote monitoring apparatus; and a notifier, configured to transmit, to the remote monitoring apparatus, a notification to notify a state in which the first monitoring apparatus is unable to acquire the first biological signal, wherein a second monitoring apparatus of the plurality of monitoring apparatuses is configured to acquire biological signals from a patient and includes:

a third holder, configured to hold the first ID and the first information for identifying the patient which is associated with the first ID;

a transmitter, configured to transmit a second biological signal to the remote monitoring apparatus; and a notifier, configured to transmit, to the remote monitoring apparatus, a notification to notify a state in which the second monitoring apparatus is unable to acquire the second biological signal and wherein the remote monitoring apparatus includes:

a second holder, configured to hold a second ID and association information for associating a screen area in a display with the second ID, wherein the second ID is a unique patient identifier;

a receiver, configured to receive a plurality of biological signals and information from the plurality of monitoring apparatuses including the first biological signal, the first ID, and the first information from the first monitoring apparatus of the plurality of monitoring apparatuses;

a detector, configured to detect the at least one of the plurality of monitoring apparatuses whose the first holder holds the first ID, and determine, based on whether the first ID is identical with the second ID, which of the biological signals is the first biological signal received from the first monitoring apparatus and what information is the first information received from the first monitoring apparatus;

and a display controller, configured to display at least one of the first biological signal and the first information on the screen area in the display based on the association information when the detector determines which of the biological signals is the first biological signal received from the first monitoring apparatus and what information is the first information received from the first monitoring apparatus;

wherein after receiving the notification from the first monitoring apparatus of the plurality of monitoring apparatuses whose the first holder holds the first ID, the remote monitoring apparatus starts to perform a detection operation for detecting and identifying which of the plurality of monitoring apparatuses is the second monitoring apparatus whose third holder holds the first ID and the display controller displays at least one of the second biological signal and the first information received from the second monitoring apparatus on the screen area in the display when the remote monitoring apparatus identified which of the plurality of monitoring apparatuses is the second monitoring apparatus whose third holder holds the first ID that corresponds to the second ID held by the remote monitoring device.

* * * * *